(12) United States Patent
Leonhardt

(10) Patent No.: US 12,226,639 B2
(45) Date of Patent: Feb. 18, 2025

(54) KLOTHO MODULATION

(71) Applicant: LEONHARDT VENTURES LLC, Corona Del Mar, CA (US)

(72) Inventor: Howard J. Leonhardt, Mission Viejo, CA (US)

(73) Assignee: LEONHARDT VENTURES LLC, Corona Del Mar, CA (US)

( * ) Notice: Subject to any disclaimer, the term of this patent is extended or adjusted under 35 U.S.C. 154(b) by 581 days.

(21) Appl. No.: 17/473,809

(22) Filed: Sep. 13, 2021

(65) Prior Publication Data
US 2021/0402184 A1    Dec. 30, 2021

Related U.S. Application Data

(63) Continuation-in-part of application No. PCT/US2020/021556, filed on Mar. 6, 2020.

(51) Int. Cl.
*A61N 1/36* (2006.01)
*A61N 1/04* (2006.01)
(Continued)

(52) U.S. Cl.
CPC ......... *A61N 1/36153* (2013.01); *A61N 1/044* (2013.01); *A61N 1/0464* (2013.01); *A61N 1/0468* (2013.01); *A61N 1/326* (2013.01); *A61N 1/36002* (2017.08); *A61N 1/36003* (2013.01); *A61N 1/36007* (2013.01); *A61N 1/3601* (2013.01); *A61N 1/36021* (2013.01); *A61N 1/36025* (2013.01); *A61N 1/36034* (2017.08); *A61N 1/36157* (2013.01); *A61N 1/3616* (2013.01); *A61N 1/36167* (2013.01);
(Continued)

(58) Field of Classification Search
CPC .. A61N 1/36153; A61N 1/044; A61N 1/0464; A61N 1/0468; A61N 1/326; A61N 1/36002; A61N 1/36003; A61N 1/36007; A61N 1/3601; A61N 1/36021; A61N 1/36025; A61N 1/36034; A61N 1/36157; A61N 1/3616; A61N 1/36167; A61N 1/36171; A61N 1/36175; A61N 1/36178; A61N 2001/083; A61N 1/0408; A61N 1/0492
See application file for complete search history.

(56) References Cited

U.S. PATENT DOCUMENTS

| 4,976,733 A | 12/1990 | Girardot |
| 9,173,811 B2 | 11/2015 | Greiner et al. |

(Continued)

FOREIGN PATENT DOCUMENTS

| WO | 2014/172693 A2 | 1/2014 |
| WO | 2016/135295 A1 | 9/2016 |
| WO | 2017/142948 A1 | 8/2017 |

OTHER PUBLICATIONS

Andringa et al. "Role of Hypoxia-Inducible Factors in Acute Kidney Injury" Nephron Clin Pract (Sep. 2014) 127: 70-74; doi.org/10.1159/000363669.
(Continued)

*Primary Examiner* — Eugene T Wu
(74) *Attorney, Agent, or Firm* — TraskBritt

(57) ABSTRACT

Described is a low voltage, pulsed electrical stimulation device for upregulating expression of klotho, a useful protein, by tissues. Also described are methods of enhancing expression of klotho in cells.

20 Claims, 19 Drawing Sheets

(51) Int. Cl.
*A61N 1/32* (2006.01)
*A61N 1/08* (2006.01)

(52) U.S. Cl.
CPC ..... *A61N 1/36171* (2013.01); *A61N 1/36175* (2013.01); *A61N 1/36178* (2013.01); *A61N 2001/083* (2013.01)

(56) References Cited

U.S. PATENT DOCUMENTS

| | | | |
|---|---|---|---|
| 9,855,418 | B2 | 1/2018 | Haralambidis |
| 9,987,326 | B2 | 6/2018 | Koeffler et al. |
| 10,646,644 | B2 | 5/2020 | Leonhardt et al. |
| 10,960,206 | B2 | 3/2021 | Leonhardt et al. |
| 11,110,274 | B2 | 9/2021 | Leonhardt |
| 2003/0220556 | A1 | 11/2003 | Porat et al. |
| 2009/0132010 | A1 | 5/2009 | Kronberg |
| 2009/0240304 | A1* | 9/2009 | Blum ............... A61N 1/326 607/2 |
| 2017/0266371 | A1* | 9/2017 | Leonhardt ............ A61N 1/326 |
| 2018/0043159 | A1 | 2/2018 | Hassan et al. |
| 2018/0064935 | A1 | 3/2018 | Leonhardt et al. |
| 2018/0193646 | A1* | 7/2018 | Fostick ............... A61N 1/20 |
| 2019/0022389 | A1 | 1/2019 | Leonhardt |
| 2019/0125932 | A1 | 5/2019 | Leonhardt et al. |
| 2019/0255321 | A1* | 8/2019 | Planard-Luong ....... H03K 7/02 |
| 2019/0290541 | A1 | 9/2019 | Greiner et al. |
| 2020/0324106 | A1 | 10/2020 | Leonhardt |
| 2021/0228870 | A1 | 7/2021 | Leonhardt |

OTHER PUBLICATIONS

Dalton et al. "New Insights into the Mechanism of Action of Soluble Klotho." Frontiers in endocrinology vol. 8 323. Nov. 17, 2017, doi:10.3389/fendo.2017.00323.

Dermaku-Sopjani et al. "Significance of the anti-aging protein Klotho" Molecular Membrane Biology, 30:8, 369-385 (Aug. 2013), DOI: 10.3109/09687688.2013.837518.

Drew et al. "Association between Soluble Klotho and Change in Kidney Function: The Health Aging and Body Composition Study" J Am Soc Nephrol Jun. 2017, 28(6):1859-1866; DOI: doi.org/10.1681/ASN.2016080828.

Floege et al. "A New Look at Platelet-Derived Growth Factor in Renal Disease" J Am Soc Nephrol (Jan. 2008), 19(1):12-23; DOI: doi.org/10.1681/ASN.2007050532.

Fu et al. "Loss of Klotho in CKD Breaks One's Heart" J Am Soc Nephrol Oct. 2015, 26 (10) 2305-2307; DOI: https://doi.org/10.1681/ASN.2015020200.

Golembiewska et al. "The Role of Klotho Protein in Chronic Kidney Disease: Studies in Animals and Humans" Current Protein & Peptide Science vol. 17, Issue 8, 2016; DOI: 10.2174/1389203717666160526123646.

Grange et al. "Urinary Extracellular Vesicles Carrying Klotho Improve the Recovery of Renal Function in an Acute Tubular Injury Mode" Molecular Therapy vol. 28 No 2 490-502 (Feb. 2020) (with Supplemental Information) https://doi.org/10.1016/j.ymthe.2019.11.013.

Gutierrez et al. "a-Klotho and Kidney Function Decline: An Important Step Forward in Understanding the Link Between Mineral Metabolism and Kidney Disease Progression" Am J Kidney Dis. (Jun. 2013) 61(6):855-857.

Hasegawa et al. "Recent advances in renal regeneration." F1000Research vol. 8 F1000 Faculty Rev-216. Feb. 25, 2019, doi:10.12688/f1000research.17127.1.

Hu et al. "Recombinant a-Klotho may be prophylactic and therapeutic for acute to chronic kidney disease progression and uremic cardiomyopathy" Kidney International Basic Research vol. 91, Issue 5, p. 1104-1114 (Jan. 2017); DOI:https://doi.org/10.1016/j.kint.2016.10.034.

Hu et al. "Secreted klotho and chronic kidney disease" Advances in Experimental Medicine and Biology, Jan. 1, 2012, 728:126-157; DOI: 10.1007/978-1-4614-0887-1_9.

Jorge et al. "Klotho deficiency aggravates sepsis-related multiple organ dysfunction" Am J Physiol Renal Physiol 316: F438-F448, (Dec. 5, 2018); doi:10.1152/ajprenal.00625.2017.

Kuro-O "The Klotho proteins in health and disease" Nat Rev Nephrol 15, 27-44 (Nov. 19, 2018); doi.org/10.1038/s41581-018-0078-3.

Lu et al. "Klotho/FGF23 Axis in Chronic Kidney Disease and Cardiovascular Disease" Kidney Dis (Jul. 2017) 3: 15-23; doi.org/10.1159/000452880.

Mitani et al. "In Vivo klotho Gene Transfer Ameliorates Angiotensin II-Induced Renal Damage" Hypertension (Apr. 2002) 39:838-843; https://doi.org/10.1161/01.HYP.0000013734.33441.EA.

Mostafidi et al. "Serum Klotho Levels in Trained Athletes", Nephro-Urol Mon. (Jan. 2016); 8(1):e30245. doi: 10.5812/numonthly.30245.

Pastor et al. "Treating Systemic Klotho Deficiency" Am J Nephrol (Apr. 2019) 49:410-412; doi.org/10.1159/000499864.

Seo et al. "Renal Klotho expression in patients with acute kidney injury is associated with the severity of the injury" The Korean Journal of Internal Medicine (Jul. 2015); 30(4):489-495.

Takenaka et al. "[OP.4B.02] Klotho Supplementation Attenuates Blood Pressure and Oxidative Stress in Diabetes" Journal of Hypertension Sep. 2017—vol. 35—Issue—p e38; doi: 10.1097/01.hjh.0000523076.42214.98.

Takenaka et al. "Klotho Ameliorates Medullary Fibrosis and Pressure Natriuresis in Hypertensive Rat Kidneys." Hypertension (Dallas, Tex. : 1979) vol. 72,5 (Nov. 2018): 1151-1159 doi: 10.1161/HYPERTENSIONAHA.118.1117.

Vervloet et al. "Fibroblast growth factor-23 and Klotho in chronic kidney disease" Kidney International Supplements vol. 1, Issue 4, p. 130-135, Sep. 1, 2011; DOI: https://doi.org/10.1038/kisup.2011.29.

Wang et al. "Correlation between Soluble a-Klotho and Renal Function in Patients with Chronic Kidney Disease: A Review and Meta-Analysis", BioMed Research International, vol. 2018, Article ID 9481475, 12 pages, (Aug. 2018). https://doi.org/10.1155/2018/9481475.

Zhou et al. "Klotho gene deficiency causes salt-sensitive hypertension via monocyte chemotactic protein-1/CC chemokine receptor 2-mediated inflammation" Journal of the American Society of Nephrology : JASN vol. 26,1 (Jan. 2015): 121-32. doi:10.1681/ASN.2013101033.

Zhou et al. "Sonic hedgehog signaling in kidney fibrosis: a master communicator" Science China. Life sciences vol. 59,9 (Sep. 2016): 920-9. doi:10.1007/s11427-016-0020-y.

Zou et al. "The role of klotho in chronic kidney disease." BMC nephrology vol. 19,1 285. Oct. 22, 2018, doi:10.1186/s12882-018-1094-z.

Zununi et al. "Klotho and Renal Fibrosis," Nephro-Urol Mon. (Nov. 2013) 5(5):946-948. doi: 10.5812/numonthly.16179.

Zhou et al. "Advance of Stem Cell Treatment for Traumatic Brain Injury" Front. Cell. Neurosci., (Aug. 13, 2019): doi.org/10.3389/fncel.2019.00301.

Zhu et al. "Klotho controls the brain-immune system interface in the choroid plexus" E11388-E11396 PNAS, vol. 115, No. 48, www.pnas.org/cgi/doi/10.1073/pnas.1808609115 accessed Apr. 12, 2019.

Alves et al. "A mesenchymal stromal cell gene signature for donor age" PLoS One. 2012;7(8):e42908. doi: 10.1371/journal.pone.0042908. Epub Aug. 23, 2012. PMID: 22927939; PMCID: PMC3426516.

Bowser et al. "Effects of the activin A-myostatin-follistatin system on aging bone and muscle progenitor cells" Exp Gerontol. Feb. 2013;48(2):290-7. doi: 10.1016/j.exger.2012.11.004. Epub Nov. 21, 2012. PMID: 23178301; PMCID: PMC3678732.

Chen et al. "Regenerative hair waves in aging mice and extrafollicular modulators Follistatin, Dkk1, and Sfrp4" J Invest Dermatol. Aug. 2014;134(8):2086-2096. doi: 10.1038/jid.2014.139. Epub Mar. 11, 2014. PMID: 24618599; PMCID: PMC4102635.

(56) References Cited

OTHER PUBLICATIONS

Dermaku-Sopjani et al. "Klotho-Dependent Role of 1,25(OH)2D3 in the Brain" Neurosignals. Mar. 31, 2021;29(1):14-23. doi: 10.33594/000000352. PMID: 33784444.

Garcia et al. "1,25(OH)2vitamin D3 stimulates myogenic differentiation by inhibiting cell proliferation and modulating the expression of promyogenic growth factors and myostatin in C2C12 skeletal muscle cells" Endocrinology. Aug. 2011;152(8):2976-86. doi: 10.1210/en.2011-0159. Epub Jun. 14, 2011. PMID: 21673099; PMCID: PMC3138228.

Negaresh et al. "The effect of resistance training on quadriceps muscle vol. and some growth factors in elderly and young men" Adv Gerontol. 2017;30(6):880-887. PMID: 29608833.

Noguchi et al. "Alteration of skin wound healing in keratinocyte-specific mediator complex subunit 1 null mice" PLoS One. Aug. 14, 2014;9(8):e102271. doi: 10.1371/journal.pone.0102271. PMID: 25122137; PMCID: PMC4133190.

Ziaaldini et al. "Exercise training increases anabolic and attenuates catabolic and apoptotic processes in aged skeletal muscle of male rats" Exp Gerontol. Jul. 2015; 67:9-14. doi: 10.1016/j.exger.2015.04.008. Epub Apr. 21, 2015. PMID: 25910622.

Apel et al. (2010), Effect of locally delivered IGF-1 on nerve regeneration during aging: an experimental study in rats, Muscle & nerve, 41(3), 335-341. doi.org/10.1002/mus.21485.

Ayden et al. "Focusing of electromagnetic waves by a left-handed metamaterial flat lens" Optics Express (Oct. 31, 2005) 13(22):8753-8759.

Back et al. "Endogenous Calcification Inhibitors in the Prevention of Vascular Calcification: A Consensus Statement From the COST Action EuroSoftCalcNet" Front. Cardiovasc. Med., 918 Jan. 2019): doi.org/10.3389/fcvm.2018.00196.

Bourdillon et al. "Electromagnetic Brain Stimulation in Patients With Disorders of Consciousness" Front. Neurosci., (Mar. 18, 2019): doi.org/10.3389/fnins.2019.00223.

Bre et al. "Prevention of bioprosthetic heart valve calcification: strategies and outcomes". Curr Med Chem. 2014;21(22):2553-64. doi: 10.2174/0929867321666131212151216. PMID: 24358975.

Brooks et al., "Bioelectric impedance predicts total body water, blood pressure, and heart rate during hemodialysis in children and adolescents" J. Ren Nutr., 18(3):304-311 (May 2008); doi: 10.1053/j.jrn.2007.11.008.

Bruggemann et al. "Effects of Neuromuscular Electrical Stimulation During Hemodialysis on Peripheral Muscle Strength and Exercise Capacity: A Randomized Clinical Trial." Arch Phys Med Rehabil. May 2017;98(5):822-831.e1. doi: 10.1016/j.apmr.2016.12.009. Epub Jan. 16, 2017. (Abstract Only).

Cai et al. "Intermedin inhibits vascular calcification by increasing the level of matrix ?—carboxyglutamic acid protein", Cardiovascular Research, vol. 85, Issue 4, Mar. 1, 2010, pp. 864-873, doi.org/10.1093/cvr/cvp366.

Caradu et al. "Endogenous Sonic Hedgehog limits inflammation and angiogenesis in the ischaemic skeletal muscle of mice". Cardiovasc Res. Apr. 1, 2018;114(5):759-770. doi: 10.1093/cvr/cvy017. PMID: 29365079.

Carboni et al. "An initial study on the effect of functional electrical stimulation in erectile dysfunction: a randomized controlled trial." Int J Impot Res. Jun. 2018; 30(3):97-101. doi: 10.1038/s41443-018-0024-8. Epub May 22, 2018. PMID: 29785045.

Chen et al. "Secreted Klotho Attenuates Inflammation—Associated Aortic Valve Fibrosis in Senescence-Accelerated Mice P1" Hypertension May 2018; 71:877-885.

Chen et al. "The Strategy to Prevent and Regress the Vascular Calcification in Dialysis Patients", BioMed Research International, vol. 2017, Article ID 9035193, 11 pages, 2017; doi.org/10.1155/2017/9035193.

Chen et al. "Deficiency in the anti-aging gene Klotho promotes aortic valve fibrosis through AMPKa-mediated activation of RUNX2." Aging Cell vol. 15, 5 (2016): 853-60. doi:10.1111/acel.12494.

Chen et al. "The Role and Mechanism of a-Klotho in the Calcification of Rat Aortic Vascular Smooth Muscle Cells." BioMed Research International vol. 2015 (2015): 194362. doi:10.1155/2015/194362.

Cheng et al. "The Role of SDF-1/CXCR4/CXCR7 in Neuronal Regeneration after Cerebral Ischemia." Frontiers in Neuroscience vol. 11 590. Oct. 24, 2017, doi:10.3389/fnins.2017.00590.

Chera et al. "Diabetes recovery by age-dependent conversion of pancreatic d-cells into insulin producers." Nature, 2014; DOI: 10.1038/nature13633.

Chernet "Transmembrane voltage potential is an essential cellular parameter for the detection and control of tumor development in a Xenopus model," Dis. Models & Mech. 6, pp. 595-607 (2013); doi:10.1242/dmm.010835.

Chu et al. "Mechanical stretch induces hair regeneration through the alternative activation of macrophages." Nature Communications, 10(1), 1524 (2019). doi.org/10.1038/s41467-019-09402-8.

Columbia "Implant Procedure Concepts—Pacemaker, ICD and CRT Overview," columbia.edu/itc/hs/medical/hickey/docs/Pacemaker,%20ICD%20and%20CRT%20Overview%20022007.pdf.

Dalise et al., "Biological effects of dosing aerobic exercise and neuromuscular electrical stimulation in rats", Sci Rep. Sep. 7, 2017; 7(1):10830.

Deng et al. "Effects of SDF-1/CXCR4 on the Repair of Traumatic Brain Injury in Rats by Mediating Bone Marrow Derived Mesenchymal Stem Cells" Cell Mol Neurobiol. Mar. 2018; 38(2):467-477. doi: 10.1007/s10571-017-0490-4. Epub May 8, 2017. Erratum in: Cell Mol Neurobiol. Apr. 2021;41(3):617-618. PMID: 28484859.

Diaco et al. "Amniotic fluid-derived stem cells as an effective cell source for transplantation therapy in stroke." Brain Circ 2015;1:119-24.

Dilorio "High-frequency external muscle stimulation in acute kidney injury (AKI): potential shortening of its clinical course" Clinical Nephrology, vol. 78—No. Suppl. Jan. 2012 (S37-S45).

Dote-Montero et al. "Predictors of Sexual Desire and Sexual Function in Sedentary Middle-Aged Adults: The Role of Lean Mass Index and S-Klotho Plasma Levels. The FIT-AGEING Study." J Sex Med. Apr. 2020;17(4):665-677. doi: 10.1016/j.jsxm.2020.01.016. Epub Feb. 20, 2020. PMID: 32089483.

Fatemi et al., "Imaging elastic properties of biological tissues by low-frequency harmonic vibration" Proceedings of the IEEE, 91(10):1503-1519 (Oct. 2003).

Ferrari "The Effect of Electrical Stimulation on Aged Skeletal Muscle Regenerative Potential" http://d-scholarship.pitt.edu/28094/1/FerrariRJ_ETD_May_31_2016_PDF.pdf.

Fukuoka et al. "Hair Regeneration Therapy: Application of Adipose-Derived Stem Cells." Current Stem Cell Research & Therapy vol. 12,7 (2017): 531-534. doi:10.2174/1574888X12666170522114307.

Geribaldi-Doldan et al. "Protein Kinase C: Targets to Regenerate Brain Injuries?" Front. Cell Dev. Biol., Mar. 20, 2019): doi.org/10.3389/fcell.2019.00039.

Ghuman et al. "Biodegradation of ECM hydrogel promotes endogenous brain tissue restoration in a rat model of stroke". Acta Biomater. Oct. 15, 2018;80:66-84. doi: 10.1016/j.actbio.2018.09.020. Epub Sep. 16, 2018. PMID: 30232030; PMCID: PMC6217851.

Guyot et al. "Pancreatic nerve electrostimulation inhibits recent-onset autoimmune diabetes". Nat Biotechnol 37, 1446-1451 (2019): doi.org/10.1038/s41587-019-0295-8.

Hopkins Medicine "Overview of Pacemakers and Implantable Cardioverter Defibrillators (ICDs)," hopkinsmedicine.org/healthlibrary/conditions/cardiovascular_diseases/overview_of_pacemakers_and_implantable_cardioverter_defibrillators_icds_85, P00234/.

Hoyer et al. "Electroconvulsive therapy enhances the anti-ageing hormone Klotho in the cerebrospinal fluid of geriatric patients with major depression." Eur Neuropsychopharmacol. Mar. 2018,28(3):428-435. doi: 10.1016/j.euroneuro.2017.12.012. Epub Dec. 20, 2017. PMID: 29274997.

Hu et al. "Renal and extrarenal actions of Klotho." Seminars In Nephrology vol. 33,2 (2013): 118-29. doi: 10.1016/j.semnephrol.2012.12.013.

International Search Report for International Application No. PCT/US2020/021556, mailed Jun. 29, 2020, 3 pages.

(56) References Cited

OTHER PUBLICATIONS

International Written Opinion for International Application No. PCT/US2020/021556, mailed Jun. 29, 2020, 4 pages.
Jayaraj et al. "Neuroinflammation: friend and foe for ischemic stroke". J Neuroinflammation 16, 142 (2019): doi.org/10.1186/s12974-019-1516-2.
Joo et al. "Various Wavelengths of Light-Emitting Diode Light Regulate the Proliferation of Human Dermal Papilla Cells and Hair Follicles via Wnt/B-Catenin and the Extracellular Signal-Regulated Kinase Pathways." Annals of Dermatology vol. 29,6 (2017): 747-754. doi:10.5021/ad.2017.29.6.747.
Kim et al. "Wnt/β-catenin and ERK pathway activation: A possible mechanism of photobiomodulation therapy with light-emitting diodes that regulate the proliferation of human outer root sheath cells." Lasers Surg Med. Dec. 2017,49(10):940-947. doi: 10.1002/lsm.22736. Epub Sep. 25, 2017. PMID: 28944964.
Kinney et al. "High intensity focused electromagnetic therapy evaluated by magnetic resonance imaging: Safety and efficacy study of a dual tissue effect based non-invasive abdominal body shaping." Lasers Surg Med. Jan. 2019;51(1):40-46. doi: 10.1002/lsm.23024. Epub Oct. 10, 2018. PMID: 30302767; PMCID: PMC6585690.
Klotho et al. "Klotho expression in osteocytes regulates bone metabolism and controls bone formation" Kidney International (2017) 92, 599-611.
Lang et al. "Therapeutic Interference with Vascular Calcification-Lessons From Klotho-Hypomorphic Mice and Beyond" Front. Endocrinol. (May 2018): doi.org/10.3389/fendo.2018.00207.
Lee et al. "Klotho ameliorates diabetic nephropathy via LKB1-AMPK-PGC1a-mediated renal mitochondrial protection" Biochemical and Biophysical Research Communications vol. 534, Jan. 1, 2021, pp. 1040-1046.
Lei "Mechanisms and Reversal of Elastin Specific Medial Arterial Calcification." (2014). All Dissertations. 1307; tigerprints.clemson.edu/all_dissertations/1307/.
Lei et al. "Efficacy of reversal of aortic calcification by chelating agents." Calcified Tissue International vol. 93,5 (2013): 426-35. doi:10.1007/s00223-013-9780-0.
Leibrock et al. "NH4CI Treatment Prevents Tissue Calcification in Klotho Deficiency" Journal of the American Society of Nephrology, Oct. 2015, 26 (10) 2423-2433.
Leon et al. "Peripheral Elevation of a Klotho Fragment Enhances Brain Function and Resilience in Young, Aging, and a-Synuclein Transgenic Mice" Cell Reports vol. 20, Issue 6, Aug. 6, 2017, pp. 1360-1371.
Li et al. "GDF10 is a signal for axonal sprouting and functional recovery after stroke" Nat Neurosci 2015; Epub Oct. 15, 2015.
Li et al. "Hair Growth Promotion Activity and Its Mechanism of Polygonum multiflorum." Evid Based Complement Alternat Med. 2015;2015:517901. doi: 10.1155/2015/517901. Epub Jul. 30, 2015. PMID: 26294926; PMCID: PMC4534627.
Lim et al. "a-Klotho Expression in Human Tissues." The Journal of Clinical Endocrinology and Metabolism vol. 100, 10 (2015): E1308-18. doi:10.1210/jc.2015-1800.
Lim et al. "Klotho: A Major Shareholder in Vascular Aging Enterprises" Int. J. Mol. Sci. 2019, 20(18), 4637; doi.org/10.3390/ijms20184637.
Liu et al. "Stem cell competition orchestrates skin homeostasis and ageing". Nature 568, 344-350 (2019); doi.org/10.1038/s41586-019-1085-7.
Malyshevskaya et al. "Role of Electrical Activity in Horizontal Axon Growth in the Developing Cortex: A Time-Lapse Study Using Optogenetic Stimulation" Plos One (2013): doi.org/10.1371/journal.pone.0082954.
Martín-González et al. "Soluble a-Klotho in Liver Cirrhosis and Alcoholism, Alcohol and Alcoholism", vol. 54, Issue 3, May 2019, pp. 204-208.
Martín-Nuñez et al. "Implications of Klotho in vascular health and disease" World J Cardiol. Dec. 26, 2014; 6(12):1262-1269.
Martinez-Redondo et al. "aKLOTHO and sTGFβR2 treatment counteract the osteoarthritic phenotype developed in a rat model". Protein Cell 11, 219-226 (2020): doi.org/10.1007/s13238-019-00685-7.
Mir et al. "IGF-1 mediated Neurogenesis Involves a Novel RIT1/Akt/Sox2 Cascade." Sci Rep 7, 3283 (2017): doi.org/10.1038/s41598-017-03641-9.
Missoum et al. "Recent Updates on Mesenchymal Stem Cell Based Therapy for Acute Renal Failure" Curr Urol 2019;13:189-199; DOI: 10.1159/000499272.
Morales-García et al. "The alkaloids of Banisteriopsis caapi, the plant source of the Amazonian hallucinogen Ayahuasca, stimulate adult neurogenesis in vitro". Sci Rep 7, 5309 (2017): doi.org/10.1038/s41598-017-05407-9.
Nakamura et al. "Eicosapentaenoic acid prevents arterial calcification in klotho mutant mice." PLoS One. Aug. 3, 2017;12(8):e0181009. doi: 10.1371/journal.pone.0181009. PMID: 28771600; PMCID: PMC5542469.
Nih et al. "Dual-function injectable angiogenic biomaterial for the repair of brain tissue following stroke". Nature Mater 17, 642-651 (2018): doi.org/10.1038/s41563-018-0083-8.
Nowak et al. "Prognostic Value and Link to Atrial Fibrillation of Soluble Klotho and FGF23 in Hemodialysis Patients" PLoS One. Jul. 3, 2014;9(7):e100688. doi: 10.1371/journal.pone.0100688.
O'Neill et al. "Recent progress in the treatment of vascular calcification." Kidney International vol. 78, 12 (2010): 1232-9. doi:10.1038/ki.2010.334.
Pai et al. "Endogenous Gradients of Resting Potential Instructively Pattern Embryonic Neural Tissue via Notch Signaling and Regulation of Proliferation." Journal of Neuroscience, 2015; 35 (10): 4366 DOI: 10.1523/JNEUROSCI.1877-14.2015.
Papaioannou et al. "Sonic Hedgehog signaling limits atopic dermatitis via Gli2-driven immune regulation" J Clin Invest. 2019; 129(8):3153-3170; doi.org/10.1172/JCI125170.
Paroni et al. "Klotho Gene and Selective Serotonin Reuptake Inhibitors: Response to Treatment in Late-Life Major Depressive Disorder". Mol Neurobiol. Mar. 2017;54(2):1340-1351. doi: 10.1007/s12035-016-9711-y. Epub Feb. 3, 2016. PMID: 26843110.
Prather et al. "Longevity factor klotho and chronic psychological stress". Translational Psychiatry, 2015; 5 (6): e585 DOI: 10.1038/tp.2015.81.
Prochazka et al., "Cocktail of Factors from Fat-derived Stem Cells Shows Promise for Critical Limb Ischemia" http://www.sciencenewsline.com/news/2016012204520017.html (Jan. 21, 2016).
Prud'homme et al. "The anti-aging protein Klotho is induced by GABA therapy and exerts protective and stimulatory effects on pancreatic beta cells." Biochem Biophys Res Commun. Dec. 2, 2017;493(4):1542-1547. doi: 10.1016/j.bbrc.2017.10.029. Epub Oct. 6, 2017. PMID: 28993191.
Qi et al. "Enhancement of neural stem cell survival, proliferation and differentiation by IGF-1 delivery in graphene oxide—incorporated PLGA electrospun nanofibrous mats" RSC Adv., 2019,9, 8315-8325.
Ranjit et al., "Potential neuroprotective role of astroglial exosomes against smoking-induced oxidative stress and HIV-1 replication in the central nervous system," Expert Opin Ther Targets. Aug. 2018; 22(8):703-714.
Rhee et al. "Neural stem cells secrete factors facilitating brain regeneration upon constitutive Raf-Erk activation." Sci Rep 6, 32025 (2016): doi.org/10.1038/srep32025.
Sachdeva et al. "Klotho and the Treatment of Human Malignancies" Cancers 2020, 12, 1665; doi: 10.3390/cancers12061665.
Sadagurski et al. "Insulin-like growth factor 1 receptor signaling regulates skin development and inhibits skin keratinocyte differentiation." Molecular and Cellular Biology vol. 26,7 (2006): 2675-87. doi:10.1128/MCB.26.7.2675-2687.2006.
Salcedo et al., "Low current electrical stimulation upregulates cytokine expression in the anal sphincter," Int. J. Colorectal Dis., Feb. 2012;27(2):221-5. doi: 10.1007/s00384-011-1324-3. Epub (Oct. 2011).
Sanchez-Nino et al. "Klotho to Treat Kidney Fibrosis" J Am Soc Nephrol 24: 687-689, 2013. doi: 10.1681/ASN.2013030294.

(56) References Cited

OTHER PUBLICATIONS

Savastano et al. "Insulin-like Growth Factor-1, Psoriasis, and Inflammation: A Ménage à Trois?" European Journal of Inflammation vol. 9 issue: 3, pp. 277-283 (2011).
Schardong et al. "Intradialytic neuromuscular electrical stimulation reduces DNA damage in chronic kidney failure patients: a randomized controlled trial," (Mar. 2018) Biomarkers, 23:5, 495-501, DOI: 10.1080/1354750X.2018.1452049.
Schardong et al. "Effects of Intradialytic Neuromuscular Electrical Stimulation on Strength and Muscle Architecture in Patients With Chronic Kidney Failure: Randomized Clinical Trial." Artif Organs. Nov. 2017;41(11):1049-1058. doi: 10.1111/aor.12886. Epub Jun. 16, 2017. (Abstract Only).
Sharma et al. "Insulin demand regulates β cell number via the unfolded protein response." Journal of Clinical Investigation, 2015; DOI: 10.1172/JCI79264.
Sieg "Mini-review of neural regeneration peptides in brain development." Journal of Stem Cell Research & Therapeutics 1 (2016): DOI: 10.15406/JSRT.2016.01.00025 Corpus ID: 14566389.
Sood et al. "Fetal Brain Extracellular Matrix Boosts Neuronal Network Formation in 3D Bioengineered Model of Cortical Brain Tissue" ACS Biomater. Sci. Eng. 2016, 2, 1, 131-140.
Stief et al. "Functional electromyostimulation of the corpus cavernosum penis—preliminary results of a novel therapeutic option for erectile dysfunction," World J. Urol. (1995) 13:243-247.
Sun et al. "Overexpression of Klotho suppresses liver cancer progression and induces cell apoptosis by negatively regulating wnt/β-catenin signaling pathway." World Journal of Surgical Oncology vol. 13 307. Oct. 24, 2015, doi:10.1186/s12957-015-0717-0.
Takenaka et al. "Klotho protein supplementation reduces blood pressure and renal hypertrophy in db/db mice, a model of type 2 diabetes" Acta Physiol (Oxf). Feb. 2019; 225(2):e13190. doi: 10.1111/apha. 13190. Epub Oct. 16, 2018.
Tang-Schomer MD. "3D axon growth by exogenous electrical stimulus and soluble factors." Brain Res. Jan. 1, 2018;1678:288-296. doi: 10.1016/j.brainres.2017.10.032. Epub Oct. 31, 2017. PMID: 29097106.
The et al. "Mechanistic Roles of Matrilin-2 and Klotho in Modulating the Inflammatory Activity of Human Aortic Valve Cells" Cells 2020, 9, 385; doi:10.3390/cells9020385.
Thurston et al. "Tumor necrosis factor and interferon-gamma down-regulate Klotho in mice with colitis". Gastroenterology. Apr. 2010;138(4):1384-94, 1394.e1-2. doi: 10.1053/j.gastro.2009.12.002. Epub Dec. 11, 2009. PMID: 20004202; PMCID: PMC3454518.
Torbus-Paluszczak et al. "Klotho protein in neurodegenerative disorders," Neurol. Sci. 39, 1677-1682 (2018): doi.org/10.1007/s10072-018-3496-x.
Van Kampen et al. "Treatment of Erectile Dysfunction by Perineal Exercise, Electromyographic Biofeedback, and Electrical Stimulation," Phys. Ther. 2003; 83(6):536-543.
Wang, et al. "Secreted klotho from exosomes alleviates inflammation and apoptosis in acute pancreatitis." American Journal of Translational Research vol. 11,6 3375-3383. Jun. 15, 2019.
Witkowski et al. "Klotho—a Common Link in Physiological and Rheumatoid Arthritis-Related Aging of Human CD4+ Lymphocytes" J Immunol (2007), 178(2):771-777; DOI: doi.org/10.4049/jimmunol. 178.2.771.
Xia et al. "Klotho Contributes to Pravastatin Effect on Suppressing IL-6 Production in Endothelial Cells." Mediators of Inflammation vol. 2016 (2016): 2193210. doi:10.1155/2016/2193210.
Xie et al. "Klotho Acts as a Tumor Suppressor in Cancers" Jul. 2013 Pathology & Oncology Research 19(4) DOI:10.1007/s12253-013-9663-8.
Xuan et al. "Changes in expression of klotho affect physiological processes, diseases, and cancer." Iranian journal of basic medical sciences vol. 21,1 (2018): 3-8.
Yaden et al. "Follistatin: a novel therapeutic for the improvement of muscle regeneration," Journal of Pharmacology and Experimental Therapeutics Mar. 13, 2014, jpet.113.211169; DOI: doi.org/10.1124/jpet.113.211169.
Yamauchi et al. "Wound healing delays in a-Klotho-deficient mice that have skin appearance similar to that in aged humans—Study of delayed wound healing mechanism" Biochemical and Biophysical Research Communications vol. 473, Issue 4, May 13, 2016, pp. 845-852.
Yarbrough et al. "Specific binding and mineralization of calcified surfaces by small peptides." Calcified Tissue International vol. 86,1 (2010): 58-66. doi:10.1007/s00223-009-9312-0.
Zhang et al. "Association of Klotho and interleukin 6 gene polymorphisms with aging in Han Chinese population." J Nutr Health Aging. Dec. 2014;18(10):900-4. doi: 10.1007/s12603-014-0470-z. PMID: 25470806.
Zhang et al. "Klotho Protein Protects Human Keratinocytes from UVB-Induced Damage Possibly by Reducing Expression and Nuclear Translocation of NF -?B." Medical Science Monitor : International Medical Journal of Experimental and Clinical Research vol. 24 8583-8591. Nov. 27, 2018, doi:10.12659/MSM.910687.
Zhao et al. "Enhancing endogenous capacity to repair a stroke-damaged brain: An evolving field for stroke research" Progress in Neurobiology vols. 163-164, Apr.-May 2018, pp. 5-26.

* cited by examiner

Follistatin: 10V, 50Hz, Square wave

IGF-1: 3.0mV, 22Hz, square wave

VEGF: 100mV, 50Hz, square wave

RANKL: 3.0mV, 2Hz, square wave

HGF: 3.5V, 10sec burst every 30 seconds, square wave

Acitivin B: 6.0mV, 150Hz, pulse width 100us, square wave

SDF-1: 3.5mV, 30Hz, square wave

SDF-1 (2nd part): 0.25mA (3.0V shown here), 100Hz, 100us pulse width, square wave Tropoelastin: 60mV, 50Hz, square wave

| KLOTHO | | OPG | KLOTHO |
|---|---|---|---|
| 0.649913 | | 21.31382 | 2.480879 |
| 496.0868 | | 3.083639 | 1.109483 |
| 1.946573 | | | |
| | | | |
| 3.416525 | | | |
| 1.736225 | | | |
| 4.655161 | | | |
| | | | |
| | | | |
| KLOTHO | | | |
| 0.649913 | | 11.02667 | |
| 1.946573 | | 17.3098 | |
| 3.416525 | | 25.70403 | |
| 1.736225 | | 26.38801 | |
| 4.655161 | | 26.14059 | |
| 2.480879 | | 21.31382 | |
| 1.564877 | | 6.895227 | |
| 0.699834 | | 3.083639 | |

FIG. 14

.* Indicates significant log fold change due to treatment.
Blue circles indicate the predicted values from the Generalized Additive Model.
Right tick marks indicate fold change.

KLOTHO MODULATION

CROSS-REFERENCE TO RELATED APPLICATIONS

This application is a continuation-in-part of PCT International Application PCT/US2020/021556, filed Mar. 6, 2020 and designating the United States, which claims the benefit of U.S. patent application Ser. No. 16/352,756 filed on Mar. 13, 2019, pending, the disclosure of each of which is hereby incorporated herein in its entirety by this reference.

TECHNICAL FIELD

The application relates generally to the field of medical devices and associated treatments, and more specifically to precise bioelectrical stimulation of a subject's tissue, possibly augmented with the administration of a composition comprising, among other things, stem cells and nutrients, useful to stimulate and treat the subject, the subject's tissue(s), the subject's organ(s), and/or the subject's cells. More specifically, the application relates to a device, programmed bioelectric signaling sequences, and associated methods for the controlled expression of Klotho via precise bioelectric signaling sequences.

BACKGROUND

Klotho protein is a kidney-secreted hormone that is known to be both membrane-bound and secreted. In man, Klotho is associated with muscle regeneration, rejuvenation, and neural protection. Loss of Klotho contributes to the aging-like features of human chronic kidney disease ("CKD") and progression of CKD. Its deficiency is also associated with degenerative processes and accelerated aging. See, e.g., Lim, Kenneth et al. "α-Klotho Expression in Human Tissues," *The Journal of Clinical Endocrinology and Metabolism* vol. 100, 10 (2015): E1308-18. doi: 10.1210/jc.2015-1800; Thurston et al. "Tumor necrosis factor and interferon-gamma down-regulate Klotho in mice with colitis," *Gastroenterology*. 2010 April; 138(4):1384-94, 1394.e1-2. doi: 10.1053/j.gastro.2009.12.002. Epub 2009 Dec. 11. PMID: 20004202; PMCID: PMC3454518.

As found by S. Ranjit et al., "Since Klotho cannot cross the blood brain barrier, it is speculated that there exist two different pools of Klotho, one secreted from kidney into serum and other secreted by the choroid plexus into cerebrospinal fluid. Due to these reasons, therapeutic use of Klotho to provide neuroprotection [to reduce neuroinflammation and oxidative damage] is limited." S. Ranjit et al., "Potential neuroprotective role of astroglial exosomes against smoking-induced oxidative stress and HIV-1 replication in the central nervous system," *Expert Opin. Ther. Targets.* 2018 August; 22(8):703-714.

Ricardo Ferrari described that the enhanced regenerative response in aged muscle following two weeks of electrical stimulation "Estim" (i.e., a Neuromuscular Stimulator (Empi 300 PV, St Paul, MN, US)) was associated with a somewhat limited, but still increased expression of Klotho (similar to that achieved from muscle contraction, e.g., exercise). Ricardo Ferrari, "The Effect of Electrical Stimulation on Aged Skeletal Muscle Regenerative Potential," d-scholarship.pitt.edu/28094/1/ FerrariRJ_ETD_May_31_2016_PDF.pdf.

Ferrari also observed a direct relationship between Klotho expression and the percentage of senescent muscle precursor cells ("MPCs"). When Klotho was inhibited through siRNA in young MPCs and aged MPCs exposed to an Estim protocol, Ferrari observed a significantly increased percentage of senescence cells. Such findings suggest that Klotho is inversely associated with senescence cells, and that Estim modulates Klotho expression in aged MPCs, and there is precedent to suggest that Klotho plays a role in inhibiting cellular senescence. See also, Dalise et al., "Biological effects of dosing aerobic exercise and neuromuscular electrical stimulation in rats," *Sci. Rep.* 2017 Sep. 7; 7(1):10830.

Using the skin and small intestine as models, others have demonstrated that Klotho enhances stem cell regenerative potential and promotes tissue healing through an inhibition of Wnt signaling activation. Recent studies demonstrated that Klotho is able to directly bind to Wnt ligands extracellularly, thereby inhibiting renal fibrosis formation.

Findings suggest that Klotho is inversely associated with senescence cells, and that Estim modulates Klotho expression in aged MPCs, and there is precedent to suggest that Klotho plays a role in inhibiting cellular senescence. See also, Dalise et al., "Biological effects of dosing aerobic exercise and neuromuscular electrical stimulation in rats," *Sci. Rep.* 2017 Sep. 7; 7(1):10830.

Schardong et al., "Intradialytic neuromuscular electrical stimulation reduces DNA damage in chronic kidney failure patients: a randomized controlled trial," *Biomarkers*, 2018, 23:5, 495-501, DOI: 10.1080/1354750X.2018.1452049, described using generic neuromuscular electrical stimulation (NMES) to reduce DNA damage in patients undergoing hemodialysis. While a step in the right direction, the further benefits of enhanced Klotho expression as described herein are still needed.

DISCLOSURE

Described is a method of using a bioelectric stimulator programmed to produce one or more bioelectric signals for stimulation of cellular tissue, wherein at least one such bioelectric signal modulates expression of Klotho by the cellular tissue, the method comprising: applying the bioelectric stimulator to the target tissue of the subject, and actuating the bioelectric stimulator to produce the programmed bioelectric signal.

Although any cellular tissue can be used, in such a method, the target tissue is typically selected from the group consisting of muscle, brain, kidney, pancreas, bone, tumor, and nerve.

Typically, the cellular tissue is that of a subject who has been diagnosed as having a condition selected from the group consisting of cancer, a tumor, atrial fibrillation, aortic valve calcification, arterial calcification, tissue calcification, erectile dysfunction, hair loss, and calcification of the breast.

The subject may be undergoing concomitant therapy (e.g., radiation treatment or chemotherapy for cancer.)

Typically, by application of the method, the amount of circulating Klotho in the subject's blood stream is increased by at least 200% over normal.

In certain embodiments, klotho expression is upregulated in the subject. Typically, this is done with a bioelectric stimulator programmed to supply at least one bioelectric signal having a frequency of from 5 to 750 Hz, and more typically selected the group consisting of 5 Hz, 10 Hz, 20 Hz, 25 Hz, 50 Hz, 75 Hz, 100 Hz, 250 Hz, 500 Hz, 750 Hz, 2,500 Hz, 100,000 Hz, 500,000 Hz, and 1 MHz. Typically, the bioelectric signal is applied to the subject for from 5 minutes to 24 hours in a day.

In certain embodiments, klotho expression is down-regulated. Typically, this is done with a bioelectric stimulator programmed to supply at least one bioelectric signal having a frequency selected from the group consisting of 25,000 Hz, 50,000 Hz, 750,000 Hz, and 1 MHz. Typically, the bioelectric signal is applied to the subject for from 5 minutes to 24 hours in a day.

Described herein is a bioelectric stimulator particularly configured to activate expression and/or release of Klotho in cellular tissue. In certain embodiments, the bioelectric stimulator is further configured to activate expression and/.or release of stromal cell-derived factor 1 ("SDF-1"), insulin-like growth factor 1 ("IGF-1"), platelet-derived growth factor ("PDGF"), follistatin, tropoelastin, and any combination thereof.

Also described is a bioelectric stimulator including: a power source (e.g., battery, capacitor, or other suitable source of electricity), and means for delivering an electrical signal to a subject's tissue (e.g., via electrode(s) or wirelessly). The bioelectric stimulator utilizes the electrical signal to precisely control protein expression in the tissue on demand.

In certain cases, the bioelectric stimulator is programmed to produce a bioelectric signal that stimulates target tissue to express and/or release Klotho polypeptide by the target tissue by utilizing a bioelectric signal comprising a biphasic square pulse at 20 Hz (at e.g., 0.1 V (100 mV)), and a 7.8 ms pulse duration for 24 hours of stimulation. In certain embodiments, such as some relating to treating the heart, the bioelectric signal stimulation will be cycling for a full 24 hours with, e.g., 6 signals in sequence, over and over.

In certain embodiments, the duration of bioelectric signal stimulation to the subject to upregulate expression of klotho stimulation is measured in minutes rather than hours. For example, a typical time of stimulation is from about 5 to 10 minutes, twice a week only. In other embodiments, stimulation times of up to 35 minutes to 1 hour are utilized.

The amount of Klotho expression enhanced by (or decreased by) the herein described system is greater than that seen with muscle stimulation or muscle contraction alone.

In certain cases, the bioelectric stimulator is further programmed to produce a bioelectric signal (to upregulate expression of SDF-1) of 30 pulses per second with a voltage of 3.5 mV, and successively alternating currents of 700 to 1500 picoamps for one minute, and again with 700 to 1500 picoamps for one minute, plus stimulated with a current of, e.g., 0.25 mA, pulse duration of 40 pulses per second, pulse width of 100 s, and frequency of 100 Hz, each signal for 40 minutes to 8 hours a day.

In certain cases, the bioelectric stimulator is further programmed to produce (to upregulate expression of PDGF) a bioelectric signal of 3 V/cm, 10 Hz at, e.g., 2 µA (0.000002 amps), and pulse duration of 0.2 ms. In certain cases, the bioelectric stimulator is further programmed to produce (to upregulate expression of PDGF) a bioelectric signal of 20 V/cm, 100 Hz at, e.g., 0.25 µA (2.5e-7 amps), and pulse duration of 40 pulses/s, width of 100 s.

In certain cases, the bioelectric stimulator is further programmed to produce (to upregulate expression of follistatin) a bioelectric signal of 10 V at 50 Hz and 100 Hz, 0.25 mA for one (1) minute.

In certain cases, the bioelectric stimulator is further programmed to produce a bioelectric signal (to upregulate expression of tropoelastin) of, e.g., 0.06 V with 50 Hz alternating electrical field and electric current at, e.g., 1 mA for 15 minutes and 3 mA for 15 minutes.

In certain cases, the bioelectric stimulator is further programmed to produce (for the expression of IGF-1) a bioelectric signal applied to the target tissue of, e.g., 3 mV with electric frequency of 22 Hz, and current of 1 mA for 15 minutes and at, e.g., 3 mA for 15 minutes.

In certain cases, a method of using the bioelectric stimulator to stimulate tissue of a subject includes connecting (directly or wirelessly) the bioelectric stimulator to the target tissue or cells of the subject. The target tissue may be selected from, e.g., the group consisting of muscle, brain, kidney, pancreas, bone, tumor, and nerve.

In certain cases, the subject is interested in body building.

In certain cases, the subject has been diagnosed as suffering from kidney failure, diabetes, bone degeneration, aging, cancer, and/or immune system dysfunction.

In certain cases, the subject has been diagnosed with cancer, a tumor, atrial fibrillation, aortic valve calcification, arterial calcification, tissue calcification, and/or calcification of the breast.

In certain cases, the subject has age-related cognitive decline. In certain cases, the subject has cognitive decline resulting from a neurodegenerative disease. In certain cases, the subject has cognitive decline resulting from traumatic brain injury. In certain cases, the subject is receiving or has received radiation treatment or chemotherapy for cancer.

A preferred system includes: a bioelectric stimulator that controls/stimulates the release/production of Klotho by a target cell or tissue. The stimulator may be associated with (e.g., connected to) the organ or tissue to be treated with a pacing infusion lead (available from Nanoscribe of Eggenstein-Leopoldshafen, Germany) or wirelessly. In certain cases, the interface with the subject's tissue may be by a conductive soft wrap.

The stimulator can be designed to externally deliver all regeneration promoting signals wirelessly to the subject's organ(s), tissue(s), and/or cells. In certain embodiments, a micro infusion pump may be included in the system to deliver other supportive substances in greater volume more quickly.

While not intending to be bound by theory, the described system utilizes precise bioelectric signaling sequences that appear to communicate with DNA and cell membranes within stimulated tissues of the subject to cause the cells to produce high volumes of the Klotho protein. Potential indications include muscle regeneration and treatment, body building, kidney regeneration and treatment, brain regeneration and treatment, cognitive function and memory improvement, skin regeneration and treatment, treatment of hair loss and regeneration of hair, wound healing, erectile dysfunction, eye regeneration and treatment, anti-aging, Multiple Sclerosis, lung regeneration and treatment, COPD, liver regeneration and treatment, hearing regeneration and treatment, blood pressure management, polyp treatment, cyst treatment, fibroid treatment, Cystic Fibrosis, heart failure, and heart valve decalcification.

BRIEF DESCRIPTION OF THE DRAWINGS

FIG. 14 is a table depicting the results of Example I.

DETAILED DESCRIPTION

In certain embodiments, described is a bandage wrap that is applied to the affected region. A micro-stimulator may be located conveniently in the bandage wrap and is utilized to distribute specific bioelectric signals to the affected tissue and nerves that regulate various protein expressions for stem cell homing, stem cell proliferation, stem cell differentiation, blood vessel formation, blood circulation improvement, muscle function repair, and DNA repair.

Figure 1:
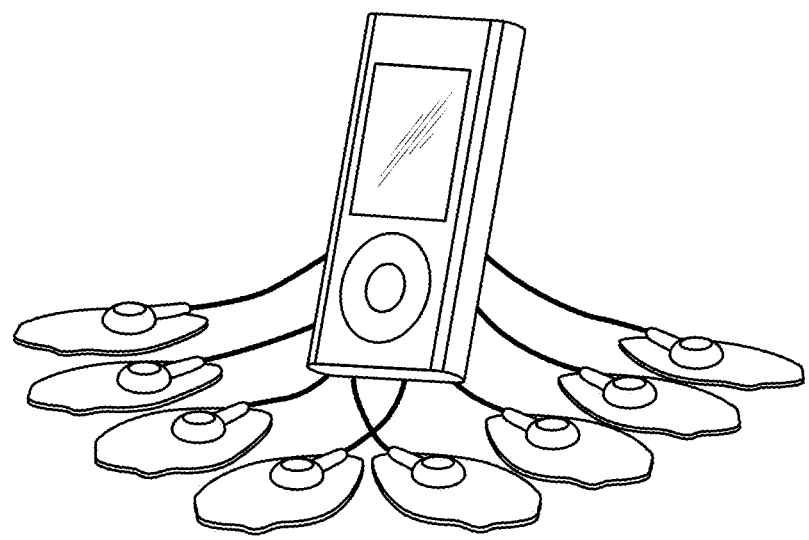
FIG. 1 depicts a programmed bioelectric stimulator for delivery to a subject connected to multiple soft conductive electrode pads.
Figure 2:
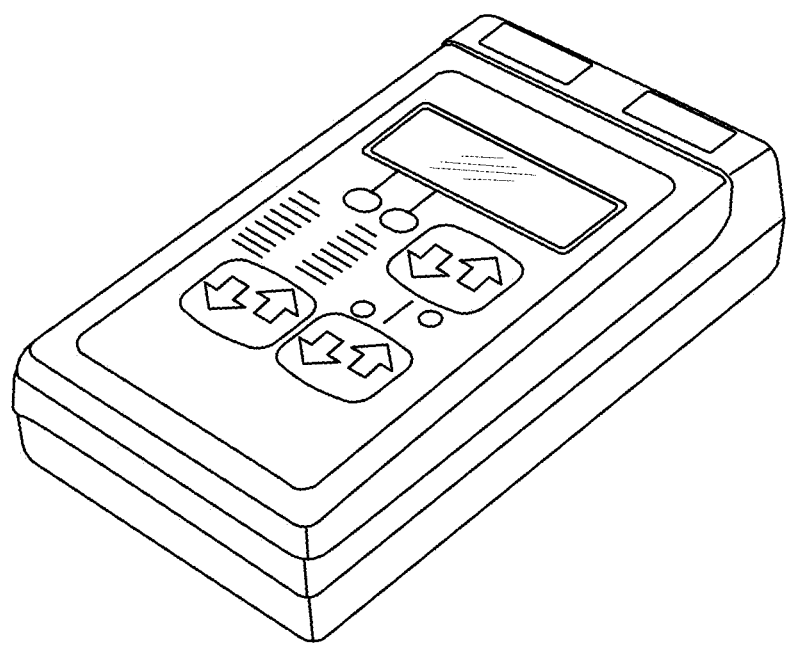
FIG. 2 depicts a programmed bioelectric stimulator as described herein.
Figure 3:
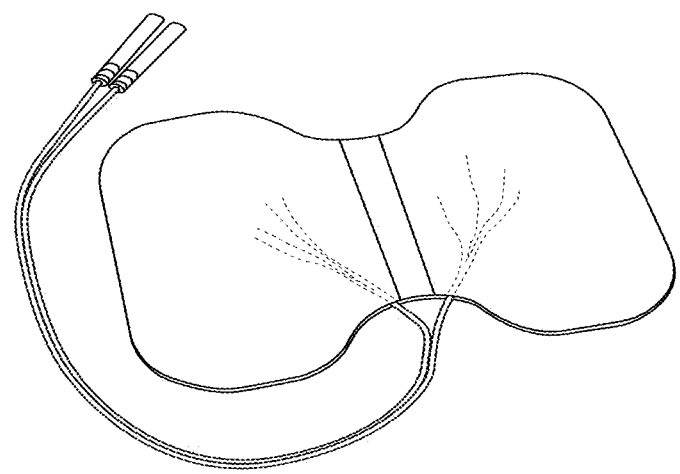
FIG. 3 depicts a conductive soft wrap for use with the system.
Figure 4:
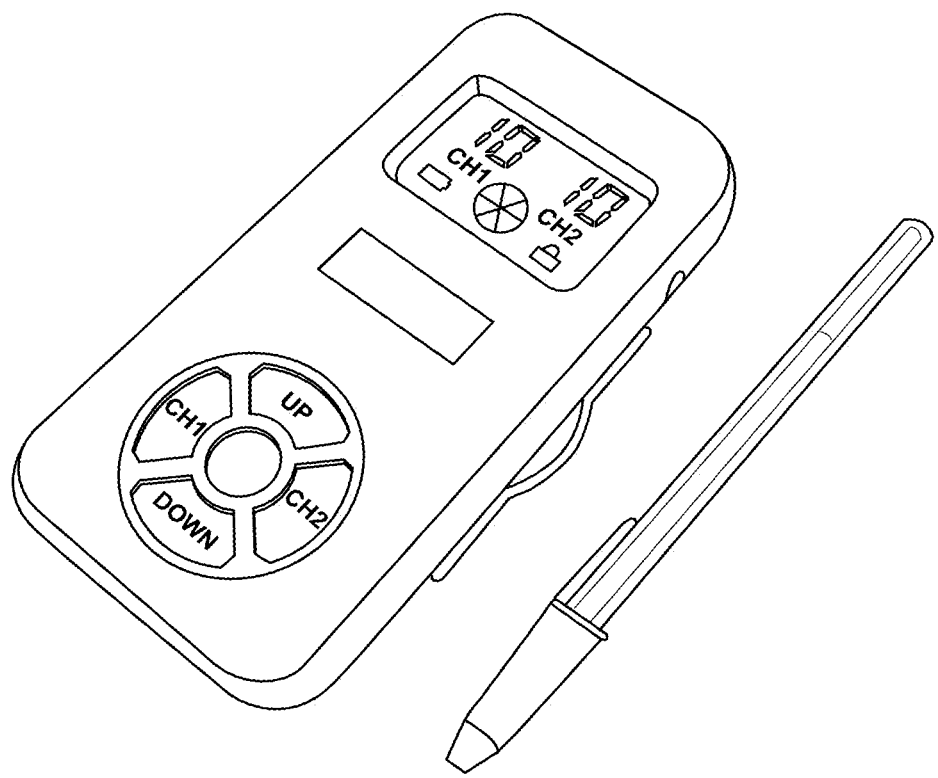
FIG. 4 depicts a programmed bioelectric stimulator depicted alongside a pen.

Referring now to FIG. 1, depicted is a stimulator for use in treating a human. The depicted device is about the size of a pen (FIG. 4) and is programmable.

Preferably, the system utilizes a bioelectric stimulator programmed to control expression and/or release of Klotho, SDF-1, IGF-1, PDGF, follistatin, and tropoelastin. See, e.g., U.S. Pat. No. 10,960,206 to Leonhardt et al. (Mar. 30, 2021) for "Bioelectric Stimulator."

Klotho is as described above. Follistatin promotes muscle growth and counteracts myostatin. SDF-1 is generally for recruiting stem cells and maturing blood vessels. IGF-1 is for DNA repair. PDGF is a second stem cell homing factor and helps tissue regeneration. Any one of the protein expression signals work well on their own for organ regeneration, but they work better together. SDF-1 is a powerful regeneration protein, as is IGF-1.

The micro voltage signal generator may be produced utilizing the same techniques to produce a standard heart pacemaker well known to a person of ordinary skill in the art. An exemplary microvoltage generator is available from Mettler of Anaheim, CA. The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal organ treatment or regeneration.

The pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

An infusion and electrode wide area patch may be constructed by cutting conduction polymer to shape, and forming plastic into a flat bag with outlet ports in strategic locations.

In certain embodiments, the bioelectric signal (or signals) is applied via a bioelectric suit. The bioelectric body suit provides bioelectric signals for increasing circulating Klotho, Follistatin, and IGF-1 bioelectric controlled protein expressions for enhanced muscle building and recovery. VEGF, PDGF and other protein expressions for improving circulation and exercise recovery. Controlled bioelectric release of tropoelastin designed to improve elasticity of skin and tendons. All of the components are typically within a comfortable stretch body suit in optimal adaptation to the subject's body.

In such a suit, the electrodes are preferably strategically located around the body. For example, electrodes are over and under the kidneys and over skeletal muscle to help stimulate circulatory Klotho production. Above and under the liver to help stimulate IGF-1 production. The electric stimulation is divided into two (2) categories starting with the sub-muscle contraction patented Leonhardt bioelectric (1) signal sequences designed to increase specific regenerative protein expressions such as klotho, follistatin, LIM muscle and IGF1 for muscle regeneration and muscle building, IGF1, sonic hedgehog and LIM for nerve regeneration, SDF1 and PDGF for stem cell homing, VEGF, eNOS, SDF1, PDGF, HIFla, CXCL5 for improving blood circulation, tropoelastin and COL17A1 for improving elasticity of tissues. Certain signaling sequences focus on reducing acute, systemic and chronic inflammation and others on pain relief Other built in electrical stimulation protocols send impulses to the deepest layers of muscles, (2) generating a natural muscle contraction.

Preferably, all of the bioelectric signaling and muscle contraction stimulation impulses are sent through 10+ pairs of electrodes that are flexible, interchangeable, anti-bacterial, and highly resistant to damage.

All the bioelectric signaling and muscle contraction stimulation impulses are sent through 10+ pairs of state-of-the-art electrodes that are flexible, interchangeable, anti-bacterial and highly resistant to damage.

Micro stimulators may be purchased or constructed in the same manner heart pacemakers have been made since the 1960s. When used with a micro infusion pump, such pumps can be purchased or produced similar to how they have been produced for drug, insulin, and pain medication delivery since the 1970s. See, also, U.S. Pat. No. 10,646,644 to Leonhardt et al. (May 12, 202)) for "Stimulator, Pump & Composition."

The programming computer can be standard laptop computer. The programming wand customary to wireless programming wands may be used to program heart pacers.

Both wireless non-invasive and/or implantable wire lead ("electrode") based means may be used to deliver the regeneration and healing promoting bioelectric signals to target organs.

A wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970s. for recharging externally implantable pacemakers.

Bioelectric stimulation can be done with the described microstimulator, which can have a pacing infusion lead with, e.g., a corkscrew lead placed/attached at, e.g., the center of the tissue to be stimulated and/or treated.

The microstimulator is actuated and runs through programmed signals to signal the release of, e.g., Klotho. In such a method, when the electrical signal includes (within 15%): a biphasic square pulse at 20 Hz, 0.1 V (100 mV), and a 7.8 ms pulse duration for 24 hours of stimulation (wherein the electrical signal is as measured three (3) mm deep into the tissue), the protein expressed and/or released is Klotho.

In such a method, when the electrical signal includes (within 15%): 10 V at 50 Hz and 100 Hz for about 12 hours each (duration 1 minute) (wherein the electrical signal is as measured three (3) mm deep into the tissue), the protein further expressed and/or released by the subject is follistatin.

In such a method, when the electrical signal includes (within 15%): 3 mV with a frequency of about 22 Hz, and a current of about 1 mA for about fifteen (15) minutes and 3 ma for about fifteen (15) minutes (duration 5 minutes) (wherein the electrical signal is as measured three (3) mm deep into the tissue), the protein further expressed and/or released by the subject is IGF-1.

For example, upregulation of IGF-1, and SDF-1 was achieved in cardiomyocytes using such signals. Upregulation of SDF-1 was achieved in pig heart. It has been found that signals for one cellular tissue work with other cellular tissues too.

Also described is a method of activating a tissue to further produce stromal cell-derived factor 1 ("SDF-1"), the method including: stimulating the (e.g., human) tissue with an electrical signal, wherein the electrical signal includes (within 15%): 30 pulses per second with a voltage of about 3.5 mV, and successively alternating currents of about 700 to 1500 picoamps for about one minute, and again with 700 to 1500 picoamps for about one minute and stimulated with current of about 0.25 mA, pulse duration of about 40 pulses/s, pulse width of about 100 s, wherein the electrical signal is as measured three (3) mm deep into the tissue. In such a method, the period of time is typically at least 24 hours. In such a method, the field strength is typically at least 0.1 V/cm.

What follows are preferred signals from the stimulator. For example, described are two PDGF expression control signals, one low voltage and one higher voltage. The test tissue is sheep heart tissue. The test cells are mesenchymal stem cells.

30% PDGF increase >3 V/cm, 10 Hz, 2 micro amps (0.000002 amps) and the pulse duration 0.2 ms.

230% PDGF increase >20 V/cm 100 Hz, 0.25 mA (2.5e-7 amps) and pulse duration of 40 pulses/s, width of 100 s.

PDGF Signal: 20 V for 1 minute, 20 mV for 10 minutes, current of 0.25 mA, pulse duration of 40 pulses/s, pulse width of 100 s, and frequency of 100 Hz for 5 minutes followed by 528 Hz for 3 minutes and 432 Hz for 3 minutes and 50 Hz for 3 minutes.

SDF-1—Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 s, and frequency of 100 Hz—each signal for 40 minutes to 8 hours a day for 2 to 36 months as needed for ideal results. Duration 7 minutes.

Stem cell proliferation signals: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours. Duration 3 minutes.

Follistatin—(muscle growth) production signal: 10V at 50 Hz and 100 Hz 0.25 mA. Duration 1 minute.

IGF-1: 3 mV with electric frequency of 22 Hz, and electric current of 1 mA for 15 minutes and 3 mA for 15 minutes. Duration 5 minutes.

An exemplary bioelectric signal sequence in humans (after Klotho) is as follows.

SDF-1 (stem cell homing signal)—5 minutes
IGF-1 signal (DNA repair)—3 minutes
Follistatin signal (myostatin antagonist) at 1 volt (not 10 volts)—3 minutes
PDGF—1 minute A week after treatment, samples can be collected for morphometric evaluation by in-situ hybridization or RT-PCR.

Among the accompanying figures are included images of the corresponding signals with the name, voltage, and frequency of each signal written on each image. The signals are to be further defined in terms of current and frequency, not voltage and frequency as shown. The voltage delivered to the cells will be different for each tissue type, but with current all of the signals can be kept constant regardless of tissue type. The device should have a current driven signal (instead of voltage driven like most other devices).

Follistatin is a powerful antagonist of myostatin. Follistatin was first isolated from the ovary and is known to suppress follicle-stimulating hormone. The system has precise bioelectric signaling sequences that have demonstrated an ability to control release of the follistatin protein in target tissue on demand.

Activin A may be produced by a bioelectric signal of 6.0 mV, pulse width 100 s, square wave, and/or 1.25 V at 5 to 10 Hz frequency. A bioelectric signal to upregulate TGF-β may also be useful in this regard too.

The upregulation of expression of various proteins is disclosed in US Patent Publication 201800649935 A1 (Mar. 8, 2018), the contents of the entirety of which are incorporated herein by this reference.

Figure 5:
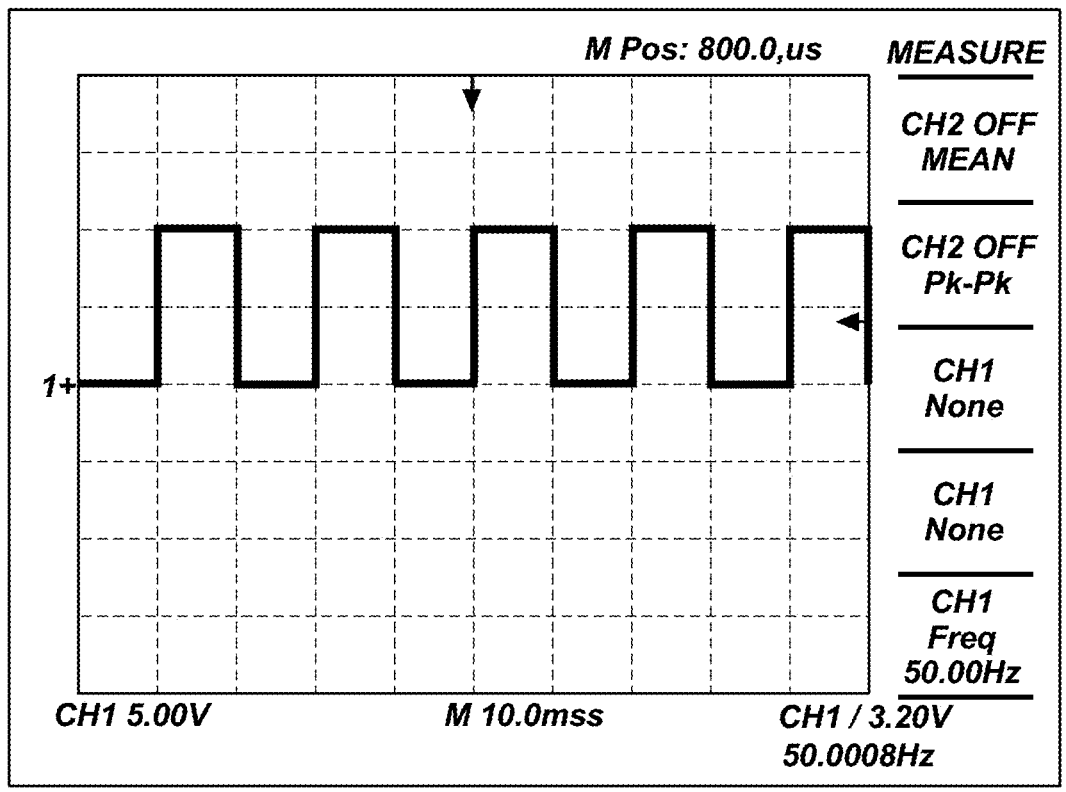
FIG. 5 depicts an image of the signal (voltage and frequency) associated with follistatin at 10 V/cm, 50 Hz, square wave.

FIG. 5 depicts an image of the signal (voltage and frequency) associated with follistatin at 10 V/cm, 50 Hz, square wave. Follistatin is a powerful antagonist of myostatin. Follistatin was first isolated from the ovary and is known to suppress follicle-stimulating hormone. The system has precise bioelectric signaling sequences that have demonstrated an ability to control release of the follistatin protein in target tissue on demand.

Figure 6:
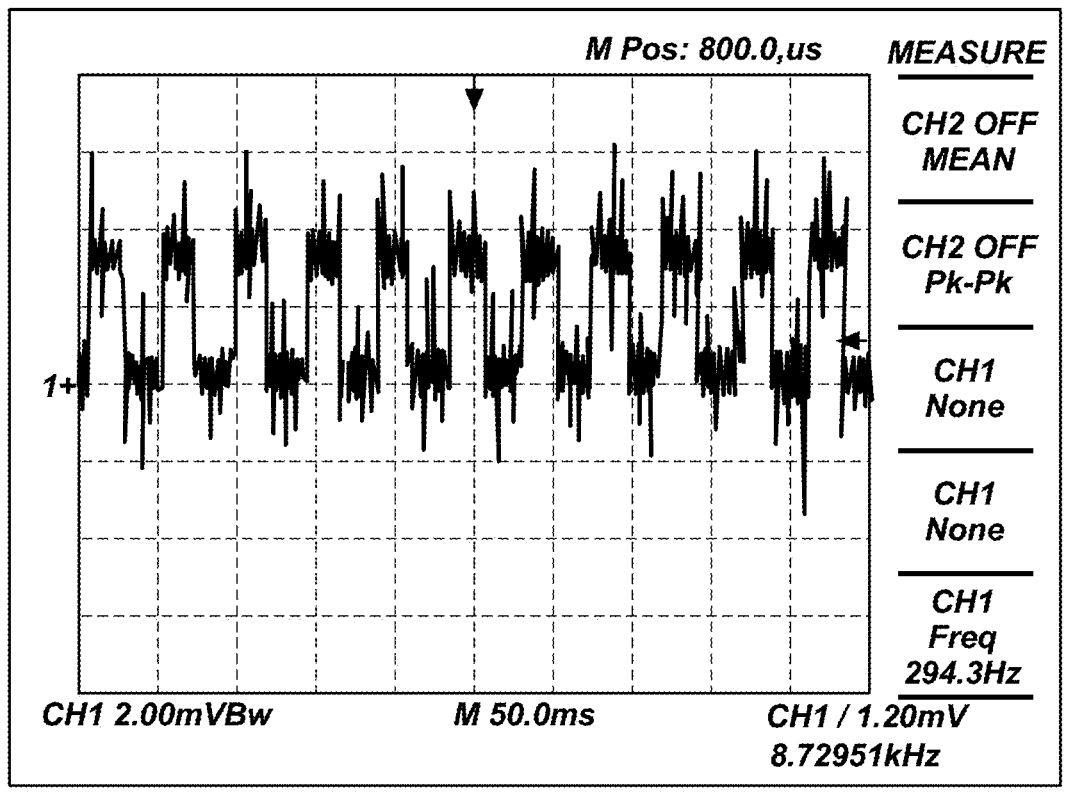
FIG. 6 depicts an image of the signal (voltage and frequency) associated with IGF-1: 3.0 mV, 22 Hz, square wave.

FIG. 6 depicts an image of the signal (voltage and frequency) associated with IGF-1: 3.0 mV, 22 Hz, square wave.

Figure 7:
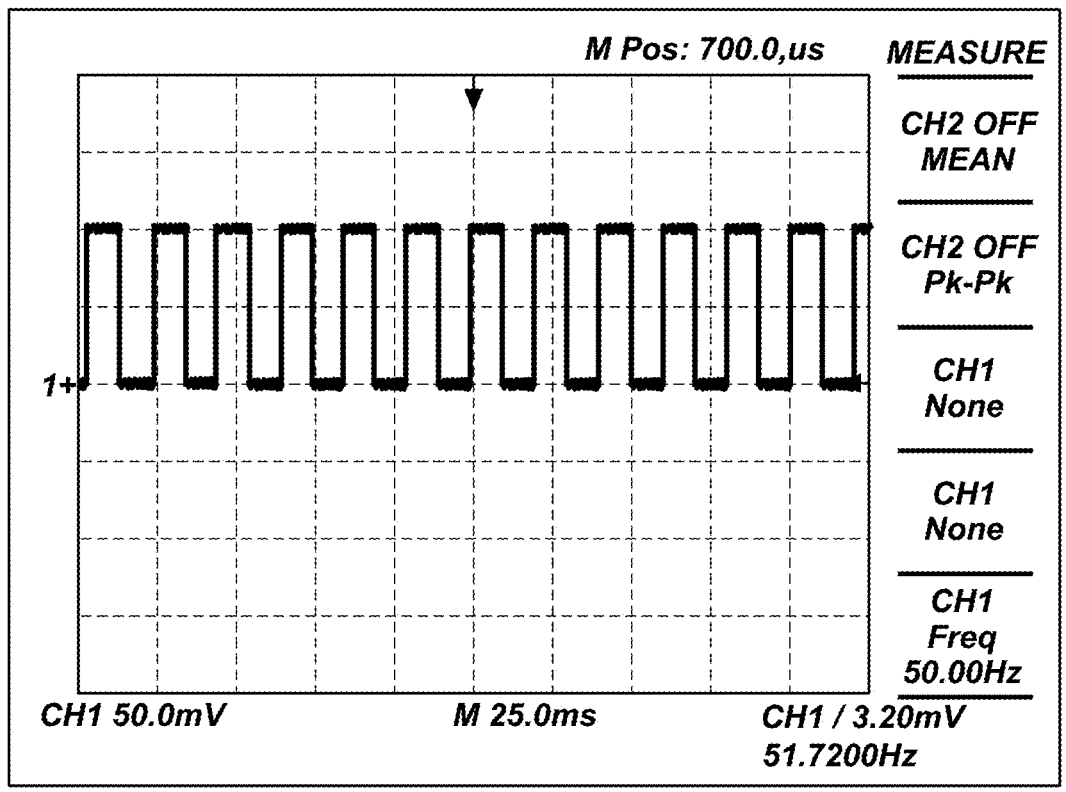
FIG. 7 depicts an image of a signal (voltage and frequency) associated with PDGF30%: 3 V/cm (100 mV here), 10 Hz, pulse width 200 µs, square wave.
Figure 8:
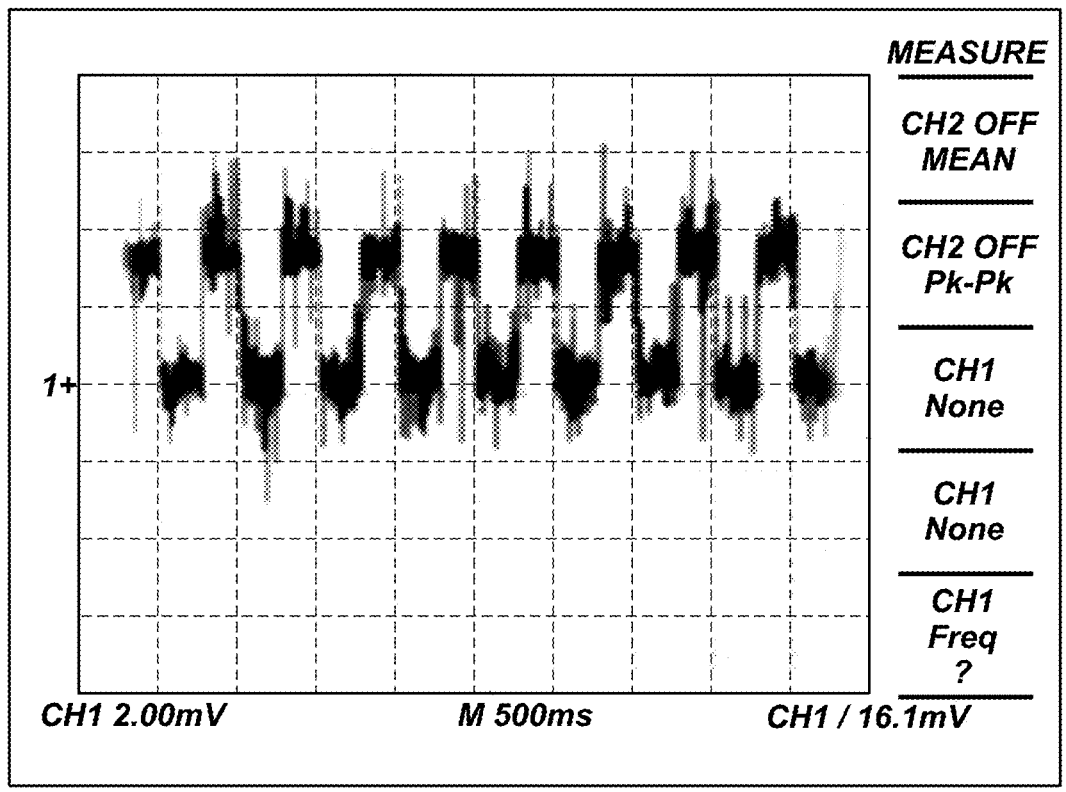
FIG. 8 depicts an image of a signal (voltage and frequency) associated with PDGF230%: 20 V/cm (7.0 V here), 100 Hz, pulse width 100 µs, square wave.

FIG. 7 depicts an image of the signal (voltage and frequency) associated with PDGF 30%: 3 V/cm (100 mV here), 10 Hz, pulse width 200 µs, square wave. FIG. 8 also depicts an image of the signal (voltage and frequency) associated with PDGF 230%: 20 V/cm (7.0 V here), 100 Hz, pulse width 100 µs, square wave.

Figure 9:
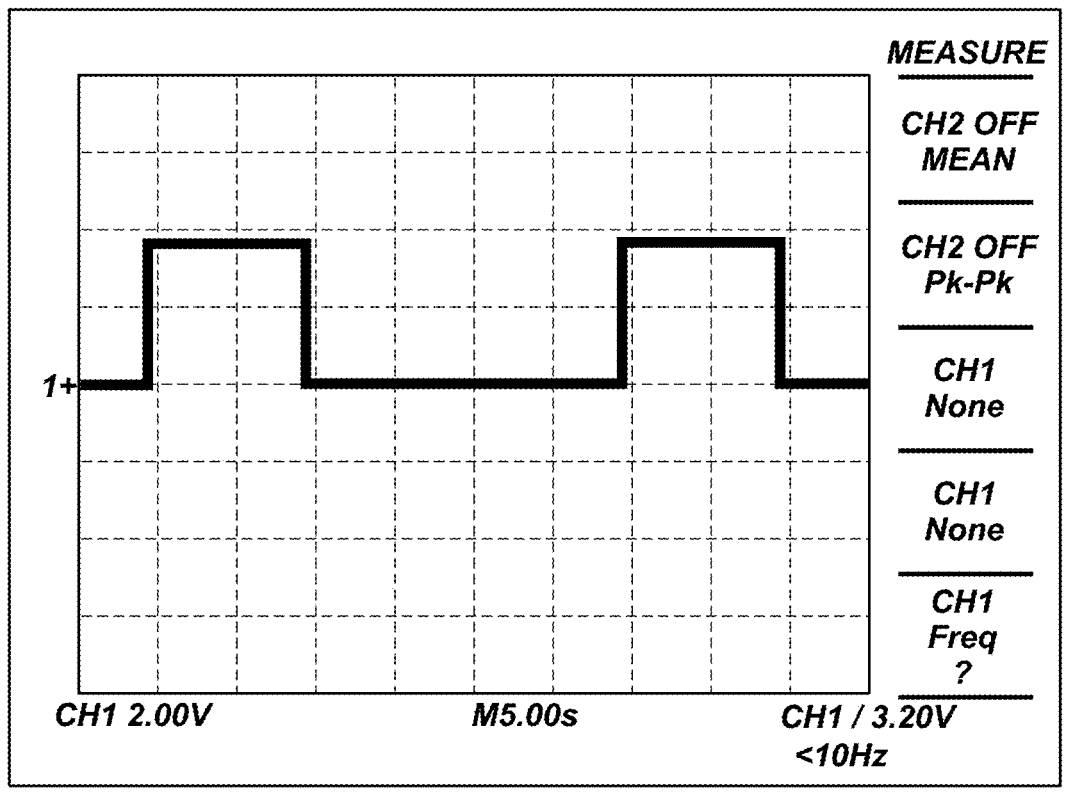
FIG. 9 depicts an image of a signal (voltage and frequency) associated with stem cell proliferation (or homing): 15 mV, 70 Hz, square wave.

FIG. 9 depicts an image of the signal (voltage and frequency) associated with stem cell proliferation: 15 mV, 70 Hz, square wave.

Figure 10:
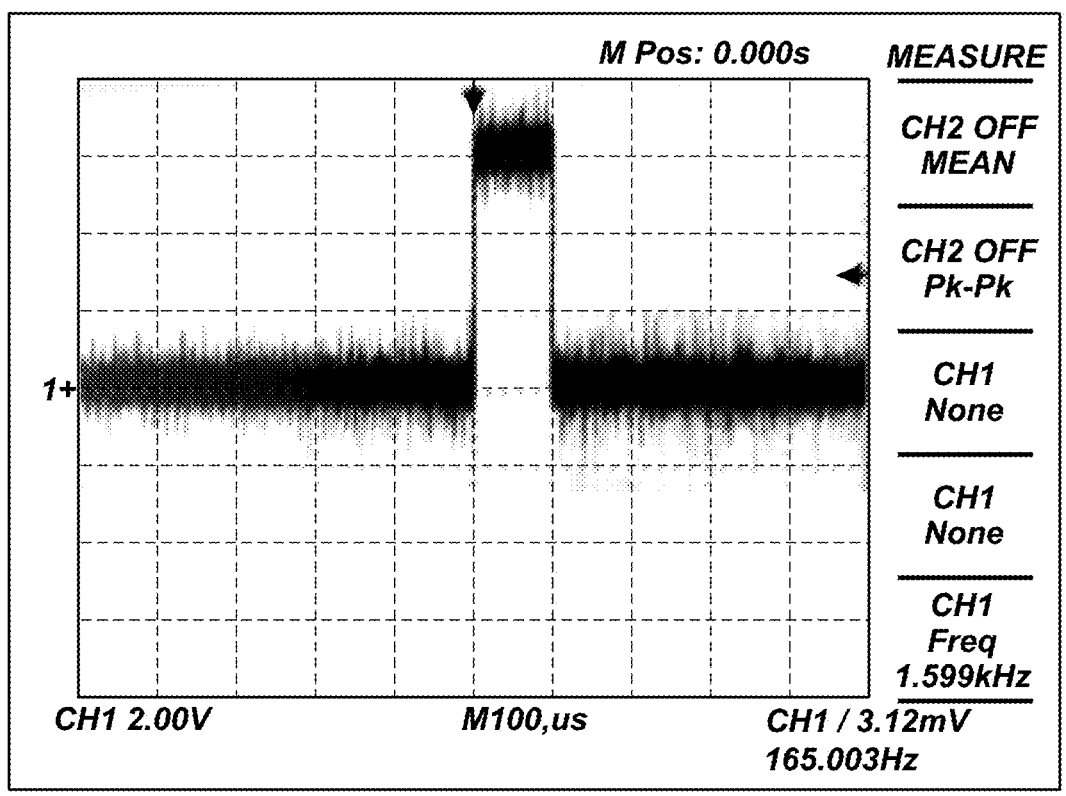
FIG. 10 depicts an image of a signal (voltage and frequency) associated with stem cell proliferation: 2.5-6.0 V (4 V here), 20 Hz, pulse width 200-700 µs, square wave.

FIG. 10 depicts an image of the signal (voltage and frequency) associated with stem cell proliferation: 2.5-6.0 V (4 V here), 20 Hz, pulse width 200-700 µs, square wave.

Figure 11:
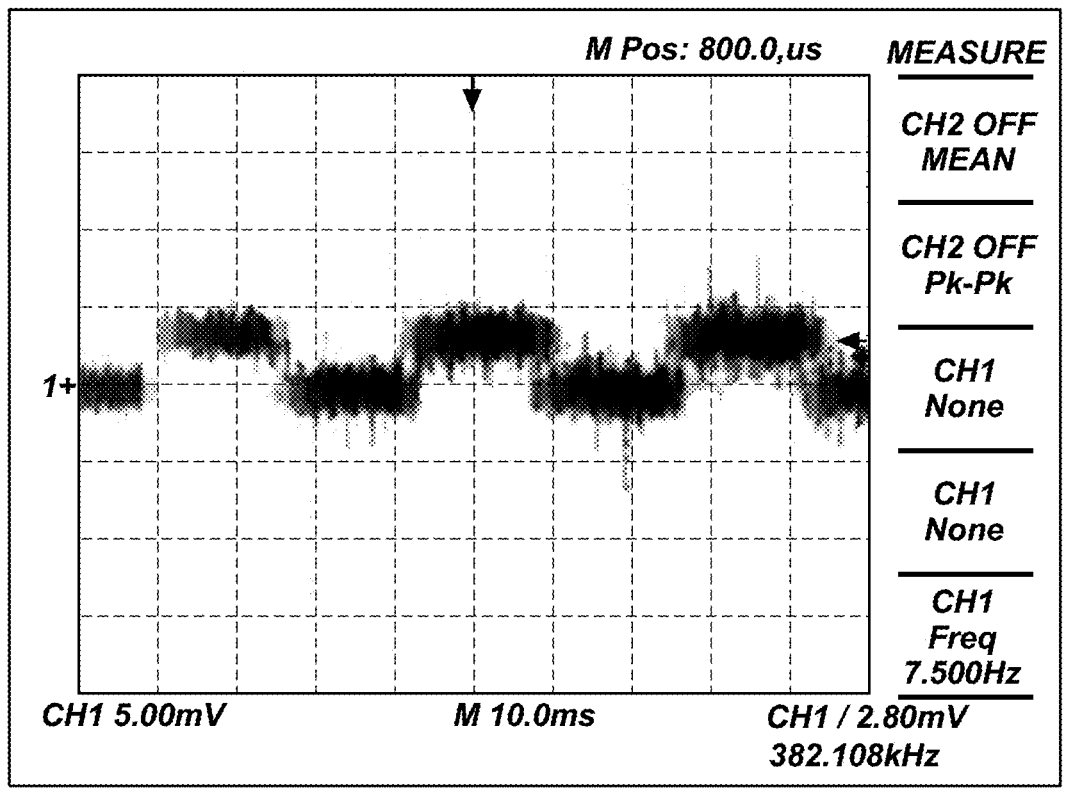
FIG. 11 depicts an image of the signal (voltage and frequency) associated with SDF-1: 3.5 mV, 30 Hz, square wave.

FIG. 11 depicts an image of the signal (voltage and frequency) associated with SDF-1: 3.5 mV, 30 Hz, square wave.

Figure 12:
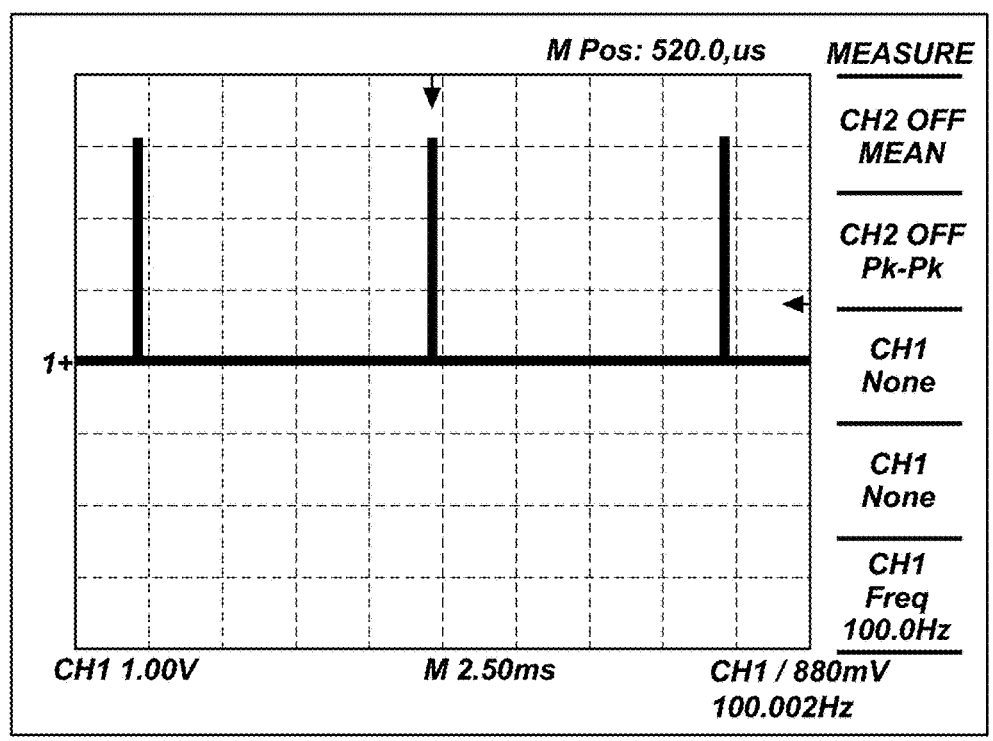
FIG. 12 depicts an image of the signal (voltage and frequency) associated with SDF-1 ($2^{nd}$ part): 0.25 mA (3.0 V shown here), 100 Hz, 100 µs pulse width, square wave.

FIG. 12 depicts an image of the signal (voltage and frequency) associated with SDF-1 ($2^{nd}$ part): 0.25 mA (3.0 V shown here), 100 Hz, 100 µs pulse width, square wave.

Figure 13:
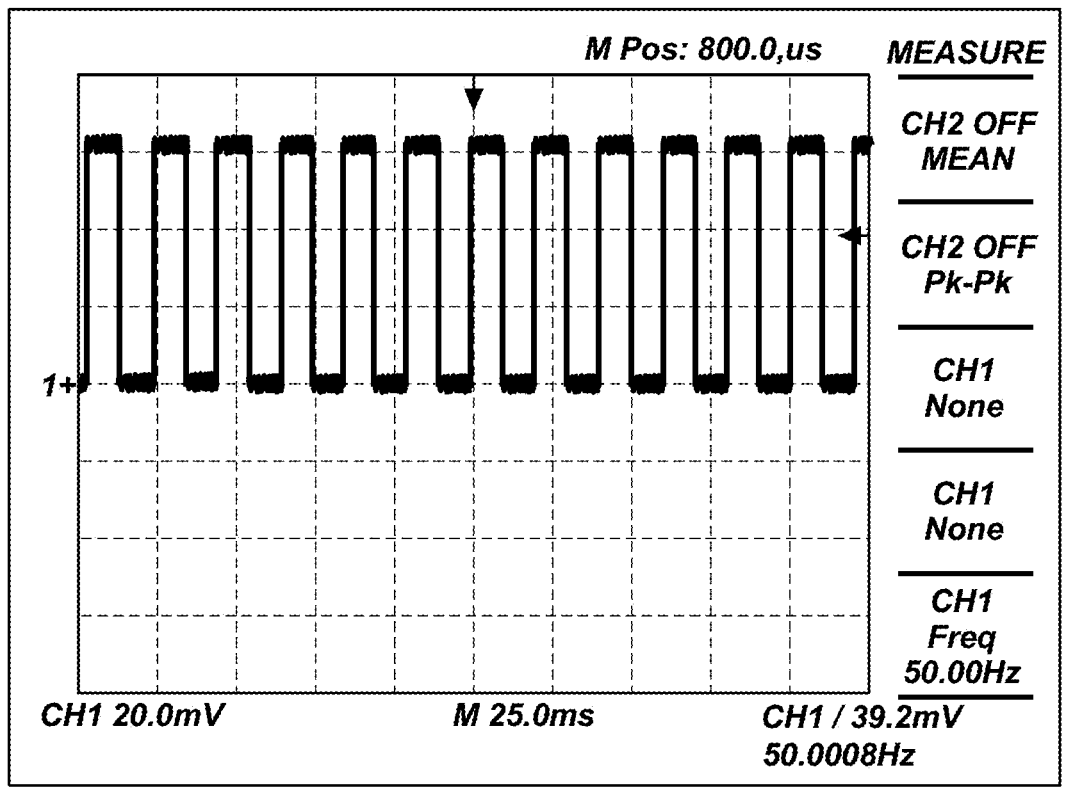
FIG. 13 depicts an image of the signal (voltage and frequency) associated with tropoelastin: 60 mV, 50 Hz, square wave.

FIG. 13 depicts an image of the signal (voltage and frequency) associated with tropoelastin: 60 mV, 50 Hz, square wave.

General Applications

In certain embodiments, described is a method of using the bioelectric stimulator described herein to stimulate tissue of a subject, the method comprising: connecting the bioelectric stimulator to the target tissue of the subject, and actuating the bioelectric stimulator to produce the programmed bioelectric signal. In such a method, the target tissue is typically selected from the group consisting of muscle, brain, kidney, pancreas, bone, tumor, liver, and/or nervous tissue. With such a method, the subject has typically been diagnosed as suffering from kidney failure, diabetes, bone degeneration, aging, cancer, and/or immune system dysfunction. In some embodiments, the subject has or is at risk of suffering from age-related cognitive decline, cognitive decline resulting from a neurodegenerative disease, and/or cognitive decline resulting from traumatic brain injury. In some embodiments, the subject is receiving or has received radiation treatment or chemotherapy for cancer.

In some embodiments, the subject has or is at risk of suffering from, for example, dementia, Alzheimer's disease, memory loss, inflammation, calcification, addiction, alcoholism, high blood pressure, aortic aneurysm recovery, lung regeneration, brain-immune interface difficulties, arthritis, vascular health, hypertension, vision recovery, teeth and gum regeneration, neurodegenerative disorders, hearing recovery, obesity, skin regeneration, aortic valve fibrosis, sun damage to the skin, psoriasis, depression and anxiety, aging, diabetic neuropathy, gut-brain health neurogenesis difficulties, pancreas and diabetes recovery, age-related inflammation, ALS, and/or Parkinson's. In some embodiments, the subject is seeking life extension (mice supplemented with klotho live 30% longer). In some embodiments, the subject is seeking to build muscle and/or aid in the recovery from muscle injury. In some embodiments, the subject is seeking to improve cognition. In some embodiments, the subject is seeking to enhance the immune system.

For example, applying a bioelectric signal to upregulate expression of klotho and a bioelectric signal to upregulate expression of follistatin to a subject contributes to the subject's liver health and/or liver regeneration. For patients with more severe liver damage, the treatment regimen may further include repeat delivery of a composition via a micro pump comprising: adipose tissue-derived stem cells and stromal fraction; selected growth factors such as Klotho, IGF1 and SDF1; Platelet Rich Fibrin (PRF); amniotic sourced regenerative fluid; exosomes; micro RNA gel; oxygenated nanoparticles; nutrient hydrogel; and alkaloids.

Applying a bioelectric signal to upregulate expression of klotho to a subject contributes to wound healing in the subject. Yamauchi et al. "Wound healing delays in α-Klotho-deficient mice that have skin appearance similar to that in aged humans—Study of delayed wound healing mechanism," *Biochemical and Biophysical Research Communications* Volume 473, Issue 4, 13 May 2016, Pages 845-852.

For treating psoriasis, a treatment regimen of a bioelectric signal for klotho (e.g., about 10 minutes), COL17A1 (for about 10 minutes), IGF-1 (for about 10 minutes) and for Sonic Hedgehog may be utilized, for an approximately 35 minute treatment three times a week for four weeks. See, Zhang, Beibei et al. "Klotho Protein Protects Human Keratinocytes from UVB-Induced Damage Possibly by Reducing Expression and Nuclear Translocation of NF-κB," *Medical Science Monitor: International Medical Journal of Experimental and Clinical Research* vol. 24 8583-8591. 27 Nov. 2018, doi:10.12659/MSM.910687; Lim et al. "Klotho: A Major Shareholder in Vascular Aging Enterprises," *Int. J. Mol. Sci.* 2019, 20(18), 4637: doi.org/10.3390/ijms20184637; Liu, N., Matsumura et al. "Stem cell competition orchestrates skin homeostasis and ageing," *Nature* 568, 344-350 (2019); doi.org/10.1038/s41586-019-1085-7; Savastano et al. "Insulin-like Growth Factor-1, Psoriasis, and Inflammation: A Ménage à Trois?" *European Journal of Inflammation* Volume: 9 issue: 3, page(s): 277-283 (2011); Sadagurski, Marianna et al. "Insulin-like growth factor 1 receptor signaling regulates skin development and inhibits skin keratinocyte differentiation," *Molecular and Cellular Biology* vol. 26, 7 (2006): 2675-87. doi:10.1128/MCB.26.7.2675-2687.2006; US Patent Application Publication US 20210228870 A1 to Leonhardt et al. (Jul. 29, 2021) for "COL17A1 Modulation"; U.S. Patent Application Publication US 20200324106 A1 to Leonhardt et al. (Oct. 15, 2020) for "Bioelectric Stimulation for Sonic Hedgehog Expression"; Papaioannou et al. "Sonic Hedgehog signaling limits atopic dermatitis via Gli2-driven immune regulation," *J. Clin. Invest.* 2019; 129(8):3153-3170: doi.org/10.1172/JCI125170; Caradu et al. "Endogenous Sonic Hedgehog limits inflammation and angiogenesis in the ischaemic skeletal muscle of mice," *Cardiovasc. Res.* 2018 Apr. 1; 114(5): 759-770. doi: 10.1093/cvr/cvy017. PMID: 29365079.

Applying a bioelectric signal to upregulate expression of klotho to a subject suffering from Parkinson's may also contributes to healing of the subject. Compare, Leon et al. "Peripheral Elevation of a Klotho Fragment Enhances Brain Function and Resilience in Young, Aging, and α-Synuclein Transgenic Mice," *Cell Reports* Volume 20, Issue 6, 6 Aug. 2017, pages 1360-1371.

For treating the subject's pancreas, applying a signal that upregulates expression of Klotho may be sufficient. Compare, Prud'homme et al. "The anti-aging protein Klotho is induced by GABA therapy and exerts protective and stimulatory effects on pancreatic beta cells," *Biochem. Biophys. Res. Commun.* 2017 Dec. 2; 493(4):1542-1547. doi: 10.1016/j.bbrc.2017.10.029. Epub 2017 Oct. 6. PMID: 28993191; Sharma et al. "Insulin demand regulates β cell number via the unfolded protein response," *Journal of Clinical Investigation,* 2015; DOI: 10.1172/JCI79264; Chera et al. "Diabetes recovery by age-dependent conversion of pancreatic δ-cells into insulin producers," *Nature,* 2014; DOI: 10.1038/nature13633. See, also, Guyot et al.

"Pancreatic nerve electrostimulation inhibits recent-onset autoimmune diabetes," *Nat. Biotechnol.* 37, 1446-1451 (2019): doi.org/10.1038/s41587-019-0295-8 and Wang, Na et al. "Secreted klotho from exosomes alleviates inflammation and apoptosis in acute pancreatitis," *American Journal of Translational Research* vol. 11, 6 3375-3383. 15 Jun. 2019. In certain instances however, this bioelectric signal regimen is utilized with a bioelectric signal that upregulates stem cell homing factors and a re-fillable micro infusion pump that may re-filled with a mixed composition of stem cells (adipose tissue derived) and support factors such a selected growth factors including SDF1, Klotho, PDGF and selected BMPs, stromal fraction, amniotic fluid, PRF, microRNA gel, selected alkaloids, nutrient hydrogel, oxygenated nano-particles and pancreatic matrix.

For treating a subject's brain, a bioelectric signal for upregulating expression of Klotho may be combined with other treatments and modalities such as exercise and those described in the incorporated U.S. Pat. No. 10,646,644 to Leonhardt et al. (May 12, 2020)) for "Stimulator, Pump & Composition"; U.S. Pat. No. 10,960,206 to Leonhardt et al. (Mar. 30, 2021) for "Bioelectric Stimulator"; U.S. Pat. No. 11,110,274 to Leonhardt (Sep. 7, 2021)) for "System and Method for Treating Inflammation"; Tang-Schomer M D. "3D axon growth by exogenous electrical stimulus and soluble factors," *Brain Res.* 2018 Jan. 1; 1678:288-296. doi: 10.1016/j.brainres.2017.10.032. Epub 2017 Oct. 31. PMID: 29097106; Malyshevskaya et al. "Role of Electrical Activity in Horizontal Axon Growth in the Developing Cortex: A Time-Lapse Study Using Optogenetic Stimulation," *PLOS ONE* (2013): doi.org/10.1371/journal.pone.0082954; Pai et al. "Endogenous Gradients of Resting Potential Instructively Pattern Embryonic Neural Tissue via Notch Signaling and Regulation of Proliferation," *Journal of Neuroscience*, 2015; 35 (10): 4366 DOI: 10.1523/JNEUROSCI.1877-14.2015; Rhee et al. "Neural stem cells secrete factors facilitating brain regeneration upon constitutive Raf-Erk activation." *Sci. Rep.* 6, 32025 (2016): doi.org/10.1038/srep32025; Diaco et al. "Amniotic fluid-derived stem cells as an effective cell source for transplantation therapy in stroke," *Brain Circ.* 2015; 1:119-24; Zhou et al. "Advance of Stem Cell Treatment for Traumatic Brain Injury," *Front. Cell. Neurosci.*, (13 Aug. 2019): doi.org/10.3389/fncel.2019.00301; Geribaldi-Doldin et al. "Protein Kinase C: Targets to Regenerate Brain Injuries?" *Front. Cell Dev. Biol.*, 20 Mar. 2019): doi.org/10.3389/fcell.2019.00039; Ghuman et al. "Biodegradation of ECM hydrogel promotes endogenous brain tissue restoration in a rat model of stroke," *Acta Biomater.* 2018 Oct. 15; 80:66-84. doi: 10.1016/j.actbio.2018.09.020. Epub 2018 Sep. 16. PMID: 30232030; PMCID: PMC6217851; Nih et al. "Dual-function injectable angiogenic biomaterial for the repair of brain tissue following stroke," *Nature Mater.* 17, 642-651 (2018): doi.org/10.1038/s41563-018-0083-8; Sood et al. "Fetal Brain Extracellular Matrix Boosts Neuronal Network Formation in 3D Bioengineered Model of Cortical Brain Tissue," *ACS Biomater. Sci. Eng.* 2016, 2, 1, 131-140; Morales-Garcia et al. "The alkaloids of Banisteriopsis caapi, the plant source of the Amazonian hallucinogen Ayahuasca, stimulate adult neurogenesis in vitro," *Sci. Rep.* 7, 5309 (2017): doi.org/10.1038/s41598-017-05407-9; Sieg, F. "Mini-review of neural regeneration peptides in brain development," *Journal of Stem Cell Research & Therapeutics* 1 (2016): DOI: 10.15406/JSRT.2016.01.00025 Corpus ID: 14566389; Jayaraj et al. "Neuroinflammation: friend and foe for ischemic stroke," *J. Neuroinflammation* 16, 142 (2019): doi.org/10.1186/s12974-019-1516-2; Zhao and Willing "Enhancing endogenous capacity to repair a stroke-damaged brain: An evolving field for stroke research," *Progress in Neurobiology* Volumes 163-164, April-May 2018, Pages 5-26; Cheng, Xi et al. "The Role of SDF-1/CXCR4/CXCR7 in Neuronal Regeneration after Cerebral Ischemia," *Frontiers in Neuroscience* vol. 11 590. 24 Oct. 2017, doi:10.3389/fnins.2017.00590; Deng et al. "Effects of SDF-1/CXCR4 on the Repair of Traumatic Brain Injury in Rats by Mediating Bone Marrow Derived Mesenchymal Stem Cells," *Cell Mol. Neurobiol.* 2018 March; 38(2):467-477. doi: 10.1007/s10571-017-0490-4. Epub 2017 May 8. Erratum in: *Cell Mol. Neurobiol.* 2021 April; 41(3):617-618. PMID: 28484859; Li et al. "GDF10 is a signal for axonal sprouting and functional recovery after stroke," *Nat. Neurosci.* 2015; Epub 2015 Oct. 15; Mir et al. "IGF-1 mediated Neurogenesis Involves a Novel RIT1/Akt/Sox2 Cascade," *Sci. Rep.* 7, 3283 (2017): doi.org/10.1038/s41598-017-03641-9; Bourdillon et al. "Electromagnetic Brain Stimulation in Patients with Disorders of Consciousness," *Front. Neurosci.*, (18 Mar. 2019): doi.org/10.3389/fnins.2019.00223; and/or Qi et al. "Enhancement of neural stem cell survival, proliferation and differentiation by IGF-1 delivery in graphene oxide-incorporated PLGA electrospun nanofibrous mats," *RSC Adv.*, 2019, 9, 8315-8325.

The described bioelectric signals may be used to treat depression, anxiety, and/or other stress-related disorders in a subject. See, e.g., Prather et al. "Longevity factor klotho and chronic psychological stress," *Translational Psychiatry,* 2015; 5 (6): e585 DOI: 10.1038/tp.2015.81, where klotho levels were found to be lower in stressed, depressed women. See, also, Paroni et al. "Klotho Gene and Selective Serotonin Reuptake Inhibitors: Response to Treatment in Late-Life Major Depressive Disorder," *Mol. Neurobiol.* 2017 March; 54(2):1340-1351. doi: 10.1007/s12035-016-9711-y. Epub 2016 Feb. 3. PMID: 26843110; Zhang W G et al. "Association of Klotho and interleukin 6 gene polymorphisms with aging in Han Chinese population," *J. Nutr. Health Aging.* 2014 December; 18(10):900-4. doi: 10.1007/s12603-014-0470-z. PMID: 25470806; Xia, Weiwei et al. "Klotho Contributes to Pravastatin Effect on Suppressing IL-6 Production in Endothelial Cells," *Mediators of Inflammation* vol. 2016 (2016): 2193210. doi:10.1155/2016/2193210; Zhu et al. "Klotho controls the brain-immune system interface in the choroid plexus," *PNAS* Nov. 27, 2018 115 (48) E11388-E11396; first published Nov. 9, 2018; and Hoyer et al. "Electroconvulsive therapy enhances the anti-ageing hormone Klotho in the cerebrospinal fluid of geriatric patients with major depression," *Eur. Neuropsychopharmacol.* 2018 March; 28(3):428-435. doi: 10.1016/j.euroneuro.2017.12.012. Epub 2017 Dec. 20. PMID: 29274997. Compare, US Patent Application Publication 20190290541 to Greiner et al. (Sep. 26, 2019) for "Implantable Electroacupuncture System and Method for Treating Depression and Similar Mental Conditions." Various mechanisms are thought to be in play, such as klotho upregulation suppresses IL6 and TNF, which are released with stress and cause depression, and/or klotho increases serotonin release which promotes brain health.

For cancer, klotho fights chronic inflammation created by chronic stress that may lead to cancer tumors. Xuan, Nguyen Thi, and Nong Van Hai. "Changes in expression of klotho affect physiological processes, diseases, and cancer," *Iranian Journal of Basic Medical Sciences* vol. 21, 1 (2018): 3-8; Xie et al. "Klotho Acts as a Tumor Suppressor in Cancers," July 2013 *Pathology & Oncology Research* 19(4) DOI:10.1007/s12253-013-9663-8; Sachdeva et al. "Klotho and the Treatment of Human Malignancies," *Cancers* 2020, 12, 1665; doi:10.3390/cancers12061665; Sun, Huidong et al. "Overexpression of Klotho suppresses liver cancer progression and induces cell apoptosis by negatively regulating wnt/β-catenin signaling pathway," *World Journal of Surgical Oncology* vol. 13 307. 24 Oct. 2015, doi:10.1186/s12957-015-0717-0.

For treating rheumatoid arthritis, a bioelectric signal for klotho may be sufficient. Witkowski et al. "Klotho—a Common Link in Physiological and Rheumatoid Arthritis-Related Aging of Human CD4+ Lymphocytes," *J. Immunol.* (2007), 178(2):771-777; DOI: doi.org/10.4049/jimmunol.178.2.771; Martinez-Redondo et al. "αKLOTHO and sTGFβR2 treatment counteract the osteoarthritic phenotype developed in a rat model," *Protein Cell* 11, 219-226 (2020): doi.org/10.1007/s13238-019-00685-7.

Klothos may be involved in inflammation and exerts antifibrogenic effects. Some of these pathways may become altered in alcoholism or liver cirrhosis. Martín-González et al. "Soluble α-Klotho in Liver Cirrhosis and Alcoholism, Alcohol and Alcoholism," Volume 54, Issue 3, May 2019, Pages 204-208.

Kidney Treatment and Prevention of Disease:

In certain embodiments, described is a method of treating a subject's kidney, the method comprising: bioelectric stimulation of muscle(s) of the subject for 30 minutes with a bioelectric stimulator programmed to produce a bioelectric signal that stimulates the muscle(s) to increase expression and/or release of Klotho polypeptide, wherein the bioelectric signal comprises a biphasic pulse at (within 15%) 20 Hz, 0.1 V, and a 7.8 ms pulse duration. Typically, such bioelectric stimulation takes place twice a week. Preferably, the muscle at least includes a quadratus lumborum of the subject.

Preferably in such a method of treating a subject's kidney, the bioelectric stimulator may be further programmed to produce and produces a bioelectric signal of 30 pulses per second with a voltage of (within 15%) 3.5 mV, square wave of 700 to 1500 picoamps.

Preferably in such a method of treating a subject's kidney, the bioelectric stimulator may be further programmed to produce and produces a bioelectric signal of (within 15%) 0.25 mA, pulse duration of 40 pulses per second, pulse width of 100 s, and frequency of 100 Hz, each signal.

Preferably in such a method of treating a subject's kidney, the bioelectric stimulator may be further programmed to produce and produces a bioelectric signal of (within 15%) 100 mV, 50 Hz, square wave.

Preferably in such a method of treating a subject's kidney, the bioelectric stimulator may be further programmed to produce and produces a bioelectric signal of (within 15%) 3 mV with electric frequency of 22 Hz, and current of 1 mA and 3 mA.

Preferably in such a method of treating a subject's kidney, the bioelectric stimulator may be further programmed to produce and produces a bioelectric signal of (within 15%) 10 V/cm, 50 Hz, square wave.

Preferably in such a method of treating a subject's kidney, the bioelectric stimulator may be further programmed to produce and produces a bioelectric signal of (within 15%): 3.5 V stimulation in 10 second bursts, one (1) burst every 30 seconds at a frequency of about 50 Hz (duration 5 minutes) (wherein an electrical signal is as measured three (3) mm deep into tissue).

Preferably in such a method of treating a subject's kidney, the bioelectric stimulator may be further programmed to produce and produces a bioelectric signal including (within 15%): alternating high-frequency and medium-frequency signals, symmetric, biphasic, trapezoid pulses, with 400-μs pulse duration and 1.5/1-s ramp-up/ramp-down duration, respectively (wherein an electrical signal is as measured three (3) mm deep into tissue).

Preferably in such a method of treating a subject's kidney, the bioelectric stimulator may be further programmed to produce and produces a bioelectric signal of (within 15%) 0.06 V with 50 Hz alternating electrical field and electric current of 1 mA.

Preferably in such a method of treating a subject's kidney, the bioelectric stimulator may be further programmed to produce and produces a bioelectric signal of (within 15%) 6 mV at 150 Hz Monophasic square wave pulse 0.1 ms.

Preferably in such a method of treating a subject's kidney, the bioelectric stimulator may be further programmed to produce and produces a bioelectric signal (eGF) of (within 15%) 10 V/cm, 500 Hz, pulse width 180 s, square wave.

In such a method of treating a subject's kidney, the bioelectric stimulator may be advantageously further programmed to produce a bioelectric signal of (within 15%) 3.0 mV, 2 Hz, square wave, alternating frequency with a current of 3 mA. In such a method of treating a subject's kidney, the bioelectric stimulator may be further programmed to produce and produces a bioelectric signal of (within 15%) 15 Hz, one (1) Gauss EM field, consisting of 5-millisecond bursts with 5-microsecond pulses followed by 200-μs pulse duration at 30 Hz and with current amplitude of 140 mA.

Such methods may be combined with other therapies, such as those disclosed in Missoum et al. "Recent Updates on Mesenchymal Stem Cell Based Therapy for Acute Renal Failure," *Curr. Urol.* 2019; 13: 189-199; DOI: 10.1159/000499272.

Heart and Heart Valve Treatment and Health

In certain embodiments, a bioelectric signal is applied to a subject in need thereof to upregulate expression of Klotho, which is used to treat or prevent heart disease, such as aortic valve fibrosis and/or heart calcification. See, e.g., Chen et al. "Deficiency in the anti-aging gene Klotho promotes aortic valve fibrosis through AMPKα-mediated activation of RUNX2," *Aging Cell* vol. 15, 5 (2016): 853-60. doi: 10.1111/acel.12494, Martín-Núñez et al. "Implications of Klotho in vascular health and disease," *World J. Cardiol.* Dec. 26, 2014; 6(12): 1262-1269, and Bre L P, McCarthy R, Wang W. "Prevention of bioprosthetic heart valve calcification: strategies and outcomes," *Curr. Med Chem.* 2014; 21(22):2553-64. doi: 10.2174/0929867321666131212151216. PMID: 24358975; and The et al. "Mechanistic Roles of Matrilin-2 and Klotho in Modulating the Inflammatory Activity of Human Aortic Valve Cells," *Cells* 2020, 9, 385; doi:10.3390/cells9020385.

After cleaning the heart valve(s), a combination of bioelectric signal sequences and biologics are applied to the valve(s), particularly bioelectric signals for SDF1 (for stem cell homing), follistatin, and klotho for leaflet regeneration. The patients are typically treated for about 20 minutes to 1 hour a month with electrodes applied to the subject's thigh muscle to release Klotho and/or other beneficial proteins, which help prevent calcification of valves and arteries going forward.

Re-calcification may be deterred by monthly (at home) bioelectric stimulation with a bioelectric signal for upregulation of Klotho of 30 minutes on, e.g., the subject's thigh muscles with non-invasive gel electrodes in order to upregulate expression and release of beneficial proteins such as klotho by the muscles.

The valves can be decalcified and regenerated with the aid of a non-invasive external chest/back wireless delivery of lithotripsy signals and regeneration signals with temporal interference method of crossing two frequencies to create an energy envelope, e.g., 2000 Hz and 2030 Hz create—at the crossing point—a 30 Hz energy envelope at the heart valve location.

This treatment may be combined with tuned harmonic resonance vibrational energy non-invasive wearable device as well to prevent plaque, calcification, blood formation on heart valves, after our procedures for preventative purposes. See, e.g., US Patent Application Publication 20190125932A1 to Leonhardt & Donofrio May 2, 2019) for "Preventing blood clot formation, calcification and/or plaque formation on blood contact surface(s)." Basically focused transmission of Mozart-like music to the heart valve that harmonically vibrates them just enough to avoid plaque formation but below the threshold for hemolysis.

The electrical surface charge of heart valves and surface protein expressions can be further modified to repel the beginning stages of plaque formation with bioelectric signaling non-invasively for prevention purposes.

In certain embodiments, the entire decalcification and calcification prevention process may be totally non-invasive with temporal interference, focused electromagnetic waves, or focused ultrasound (e.g., at 40 kHz) and peripheral bioelectric stimulation such as stimulating the subject's thigh muscle to release Klotho, which prevents calcification. See, e.g., Chen, Tianlei et al. "The Role and Mechanism of α-Klotho in the Calcification of Rat Aortic Vascular Smooth Muscle Cells," *BioMed. Research International* vol. 2015 (2015): 194362. doi:10.1155/2015/194362; Leibrock et al. "You have access NH4Cl Treatment Prevents Tissue Calcification in Klotho Deficiency," *Journal of the American Society of Nephrology*, October 2015, 26 (10) 2423-2433; Nakamura et al. "Eicosapentaenoic acid prevents arterial calcification in klotho mutant mice," *PLoS One*. 2017 Aug. 3; 12(8):e0181009. doi: 10.1371/journal.pone.0181009. PMID: 28771600; PMCID: PMC5542469; Lang et al. "Therapeutic Interference With Vascular Calcification—Lessons From Klotho-Hypomorphic Mice and Beyond," *Front. Endocrinol.* (May 2018): doi.org/10.3389/fendo.2018.00207.

Focused electromagnetic waves are described in Ayden et al. "Focusing of electromagnetic waves by a left-handed metamaterial flat lens," *Optics Express* (31 Oct. 2005) 13(22):8753-8759; Kinney B M, Lozanova P. "High intensity focused electromagnetic therapy evaluated by magnetic resonance imaging: Safety and efficacy study of a dual tissue effect based non-invasive abdominal body shaping," *Lasers Surg. Med* 2019 January; 51(1):40-46. doi: 10.1002/lsm.23024. Epub 2018 Oct. 10. PMID: 30302767; PMCID: PMC6585690.

After completion of a third cleaning with, e.g., citric acid, valves are treated to prevent re-calcification, which may be done before and after the regeneration procedure. O'Neill, W Charles, and Koba A Lomashvili. "Recent progress in the treatment of vascular calcification," *Kidney International* vol. 78, 12 (2010): 1232-9. doi:10.1038/ki.2010.334; Chen, Nai-Ching et al. "The Strategy to Prevent and Regress the Vascular Calcification in Dialysis Patients," *Biomed. Research International*, vol. 2017, Article ID 9035193, 11 pages, 2017; Lei, Yang et al. "Efficacy of reversal of aortic calcification by chelating agents," *Calcified Tissue International* Vol. 93, 5 (2013): 426-35. doi:10.1007/s00223-013-9780-0; U.S. Pat. No. 4,976,733 to Giradot (Dec. 11, 1990) for "Prevention of prosthesis calcification"; Lei, Yang "Mechanisms And Reversal Of Elastin Specific Medial Arterial Calcification" (2014). All Dissertations. 1307; tigerprints.clemson.edu/all_dissertations/1307/; Yarbrough et al. "Specific binding and mineralization of calcified surfaces by small peptides," *Calcified Tissue International* Vol. 86, 1 (2010): 58-66. doi:10.1007/s00223-009-9312-0; Yan Cai et al. "Intermedin inhibits vascular calcification by increasing the level of matrix γ-carboxyglutamic acid protein," *Cardiovascular Research*, Volume 85, Issue 4, 1 Mar. 2010, Pages 864-873, doi.org/10.1093/cvr/cvp366; Bäck et al. "Endogenous Calcification Inhibitors in the Prevention of Vascular Calcification: A Consensus Statement From the COST Action EuroSoftCalcNet" *Front. Cardiovasc. Med.*, 918 January 2019): doi.org/10.3389/fcvm.2018.00196.

Erectile Dysfunction Treatment and Prevention

In certain embodiments, the bioelectric stimulation therapy described herein is used as part of a system and/or method to treat and/or prevent erectile dysfunction in a subject. In such a case, regeneration of smooth muscle cavernosa by bioelectric stimulation is intended to spontaneously return erectilility. Stief et al. "Functional electromyostimulation of the corpus cavernosum penis—preliminary results of a novel therapeutic option for erectile dysfunction," *World J. Urol.* (1995) 13:243-247. This contrasts with prior art oral, injection therapy and/or the use of a vacuum pump where the patient is treatment dependent. van Kampen et al., "Treatment of Erectile Dysfunction by Perineal Exercise, Electromyographic Biofeedback, and Electrical Stimulation," *Phys. Ther.* 2003; 83(6):536-543.

Further, klotho levels have been associated with libido. Dote-Montero et al. "Predictors of Sexual Desire and Sexual Function in Sedentary Middle-Aged Adults: The Role of Lean Mass Index and S-Klotho Plasma Levels. The FIT-AGEING Study," *J. Sex. Med* 2020 April; 17(4):665-677. doi: 10.1016/j.jsxm.2020.01.016. Epub 2020 Feb. 20. PMID: 32089483.

In certain embodiments, the bioelectric stimulator is set to upregulate the expression of Klotho. Preferably, the upregulation is at least 200% over normal. Further preferably, the Klotho expression is upregulated so that the amount of circulating Klotho in the subject's blood stream is increased by 200%.

In certain embodiments, the treatment regimen includes the application of bioelectric signal(s) to the subject for as little as 15 minutes every other day for only 4 weeks to see results.

Secretory Klotho results in the reduction of TNFα and IFNγ, which can show anti-inflammatory properties. Klotho can interact with Wnt, which results in the inhibition of Wnt pathway activity, thus inhibiting the aging process. Torbus-Paluszczak et al., "Klotho protein in neurodegenerative disorders," *Neurol. Sci.* 39, 1677-1682 (2018): doi.org/10.1007/s10072-018-3496-x.

The bioelectric stimulator is further programmed to upregulate IGF-1 to improve nerve regeneration and neuromuscular recovery. Apel, P. J., Ma, J., Callahan, M., Northam, C. N., Alton, T. B., Sonntag, W. E., & Li, Z. (2010), Effect of locally delivered IGF-1 on nerve regeneration during aging: an experimental study in rats, *Muscle & nerve*, 41(3), 335-341: doi.org/10.1002/mus.21485.

The bioelectric stimulator is further programmed to upregulate follistatin, which promotes muscle regeneration and recovery. Follistatin is able to accomplish accelerated muscle restoration not only by leveraging the regenerative effects of myostatin inhibition but potentially through modulating inflammation. Yaden et al., "Follistatin: a novel therapeutic for the improvement of muscle regeneration," *Journal of Pharmacology and Experimental Therapeutics* Mar. 13, 2014, jpet.113.211169; DOI: doi.org/10.1124/jpet.113.211169.

In most such methods, the bioelectric stimulation may be administered to the muscle(s) subject wirelessly.

In such a method, the bioelectric stimulation may be administered to the muscle(s) via a gel tape electrode applied to the subject's skin proximate the muscle(s). In such a method, the gel tape electrode may be applied to at least one thigh of the subject.

Such a method may be helpful to a subject having been diagnosed with kidney failure, diabetes, aging, and/or cancer.

Relationship Between the Components:

The micro voltage signal generator is attached to the pacing infusion lead with, e.g., a corkscrew tip, deep vein stimulation lead (Medtronic) (e.g., for bioelectric stimulation of the brain), or conductive polymer bandage or patch to the tissue or organ to be treated. An external signal programmer may be used to program the micro voltage signal generator with the proper signals for treatment including the Klotho producing signal. The device battery may be re-chargeable with an external battery charging wand.

The essential elements are the micro voltage signal generator and the means for delivering the signal to the target tissue.

The signal generator may be external or internal. The transmission of the signal may be wireless, via liquid and/or via wires.

The tissue contact interface may be, e.g., a patch or bandage or may be via electrodes or leads. FDA cleared gel tape electrodes (Mettler) may be used for skin delivery. Electro acupuncture needles may be used to ensure the signals positively reach target tissues under the skin.

In certain embodiments, a subject's organ(s) and/or tissue (s) are first scanned or analyzed with a device to determine what his or her needs may be before treatment begins. The scanning/analysis can be by, e.g., generating mechanical vibrations at position adjacent the location to be an analyzed as described in, e.g., US 2003/0220556 A1 to Porat et al. (the contents of which are incorporated herein by this reference) and/or by measuring transmembrane voltage potential of a cell (see, e.g., Chernet & Levin, "Transmembrane voltage potential is an essential cellular parameter for the detection and control of tumor development in a *Xenopus* model," *Dis. Models & Mech.* 6, pp. 595-607 (2013); doi:10.1242/dmm. 010835), the contents of which are also incorporated herein by this reference. See, also, Brooks et al., "Bioelectric impedance predicts total body water, blood pressure, and heart rate during hemodialysis in children and adolescents," *J. Ren. Nutr.,* 18(3):304-311 (May 2008); doi: 10.1053/ j.jrn.2007.11.008, the contents of which are incorporated herein by this reference, describing the use of bioelectric impedance to evaluate the variability of blood pressure, systolic blood pressure, etc.

As used herein, "scanning" means measuring bioelectrical electrical activity of organs, sometimes by placement of a bion coil reader and transmitter in the organ, and direct that information to a computer. The computer stores the bioelectrical read measurements of diseased organs and healthy organs and makes a comparative exam classifying the organ into one category or another, which is much like a doctor using information to make a diagnosis.

Presently, the best approach for whole body and individual organ scanning is to use a combination of: a. 3D Body Scannint, b. Quantum Magnetic Resonance Scanning, c. Biofeedback scanning, d. Bioelectric scanning, e. Bion implant scanning, f Nervous system scanning, and g. Light activated cell reaction reading.

Scanners such as the Ina'Chi scanner, the Quantum Magnetic Resonance Analyzer (QMRA), the 3D Quantum Health Analyzer Scan whole body organ health 2, Body-Scan® scanner, and the "BIONic muscle spindle" are also useful.

For example, the subject is positioned for analysis with a device, preferably with a non-invasive testing device for evaluating, e.g., the autonomic nervous system, organ function(s), and risk factors associated with heart disease, diabetes, and stroke. The non-invasive testing device may analyze data from, e.g., the subject's skin galvanic response, skin color, oximeter, blood pressure, and body composition analyzer to determine hardening and thickening of the subject's arteries, the subject's heart health, exercise capacity, thyroid function, neurotransmitter balance, and multiple other markers for health. See, also, Fatemi et al., "Imaging elastic properties of biological tissues by low-frequency harmonic vibration," *Proceedings of the IEEE,* 91(10):1503-1519 (October 2003).

In an alternative embodiment, the analysis conducted by the device comprises (or further includes) detecting minute energy fields around the human body with, e.g., a "SQUID magnetometer" (SQUID is an acronym for "Superconducting Quantum Interference Device"), able to detect biomagnetic fields associated with physiological activities in the subject's body. A quantum resonant magnetic analyzer analyzes such fields. The magnetic frequency and energy of a subject's organ(s) and/or tissue(s) are collected by appropriately positioning the sensor with respect to the portion of the subject's organ(s) and/or tissue(s) to be analyzed, and after amplification of the signal by the instrument, the data are compared with standard quantum resonant spectrum of diseases, nutrition, and other indicators/markers to determine whether the sample waveforms are irregular using a Fourier approach.

Treatment may include, e.g., moving magnets or changing magnetic fields (pulsed electromagnetic fields) about the tissue and/or organ, for example, to reduce inflammation or treat pain or induce tissue growth in the subject.

The invention is further described with the aid of the following illustrative Example.

EXAMPLES

Example I—Controlling Expression and/or Release of Klotho

Twelve samples of gingiva cells were stimulated with a biphasic square pulse at 20 Hz, 0.1 V (100 mV), and a 7.8 ms pulse duration for 24 hours of stimulation. The cells were gingival fibroblasts from a 28-year-old Caucasian male (internet at atcc.org/en/Products/All/CRL-2014.aspx), which were passaged less than 8 times. RT-PCR was used to measure results before and after the described bioelectric stimulation. Results: Klotho expression up an average of 248% (n=5) and as high as 465% in skeletal muscle cells (see FIG. 14).

Example II—Controlling Expression and/or Release of Klotho

Samples of cultured cells (e.g., urinary smooth muscle cells) were stimulated for 30 minutes using a square, biphasic waveform at 50% duty (1 V at 5 Hz to 1 MHz). Bioelectric stimulation was applied to the cultured cells in vitro using a commercially available constant voltage waveform generator RIGOL LXI 1022Z (Beaverton, OR, US) via a 6-well stimulating plate interface (IONOPTIX, Westwood, MA, US).

RT-qPCR was used to measure klotho expression at the varying frequencies. qPCR triplicate measures with standard deviations above 1 were removed.

Figure 15:
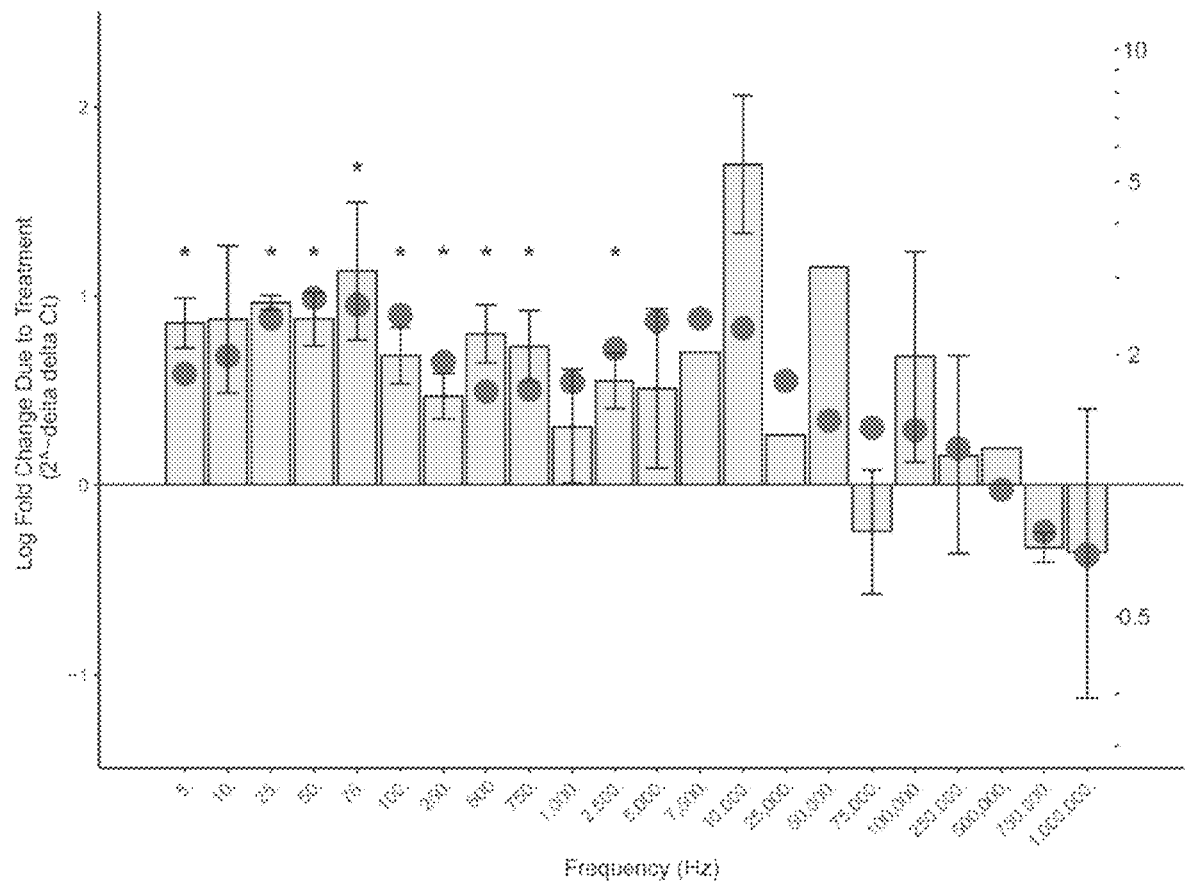
FIGS. 15 and 16 graphically depict the results of Example II.
Figure 16:
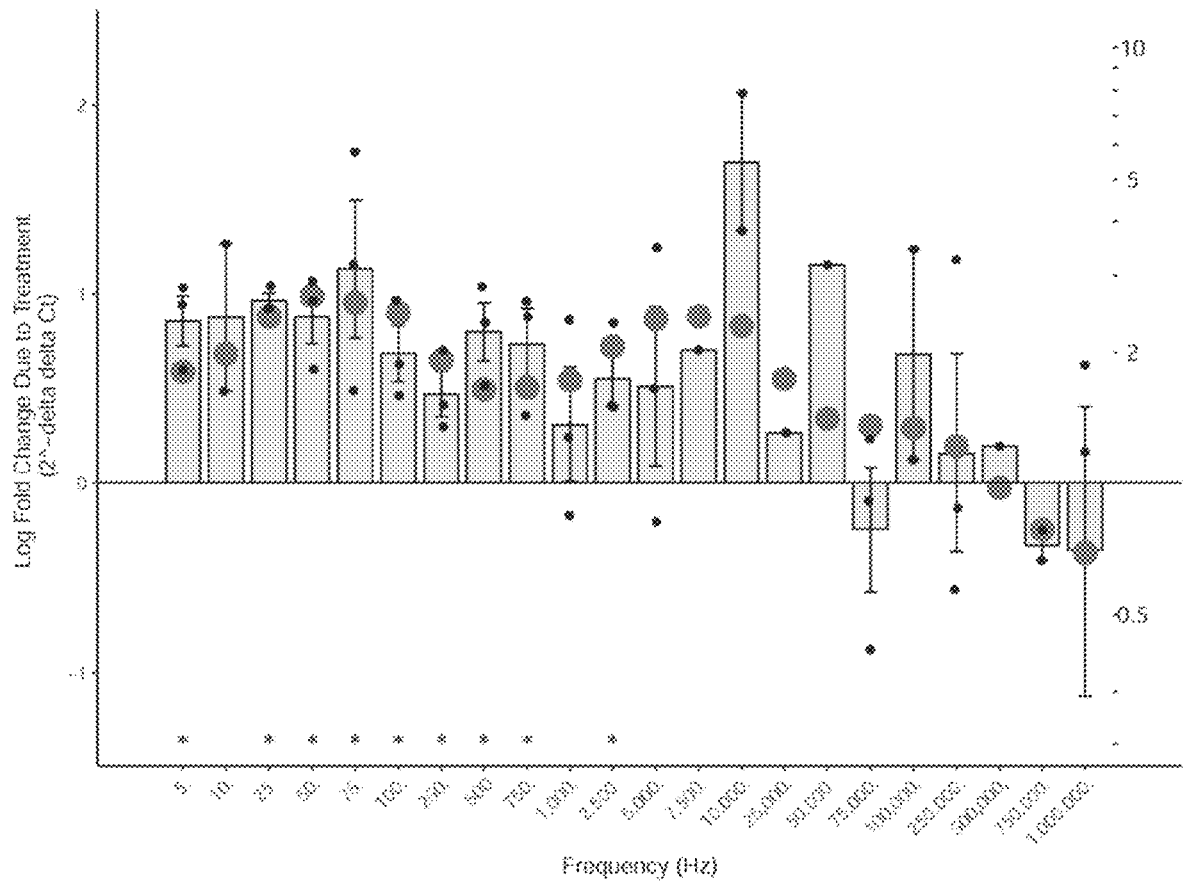
Figure 17:
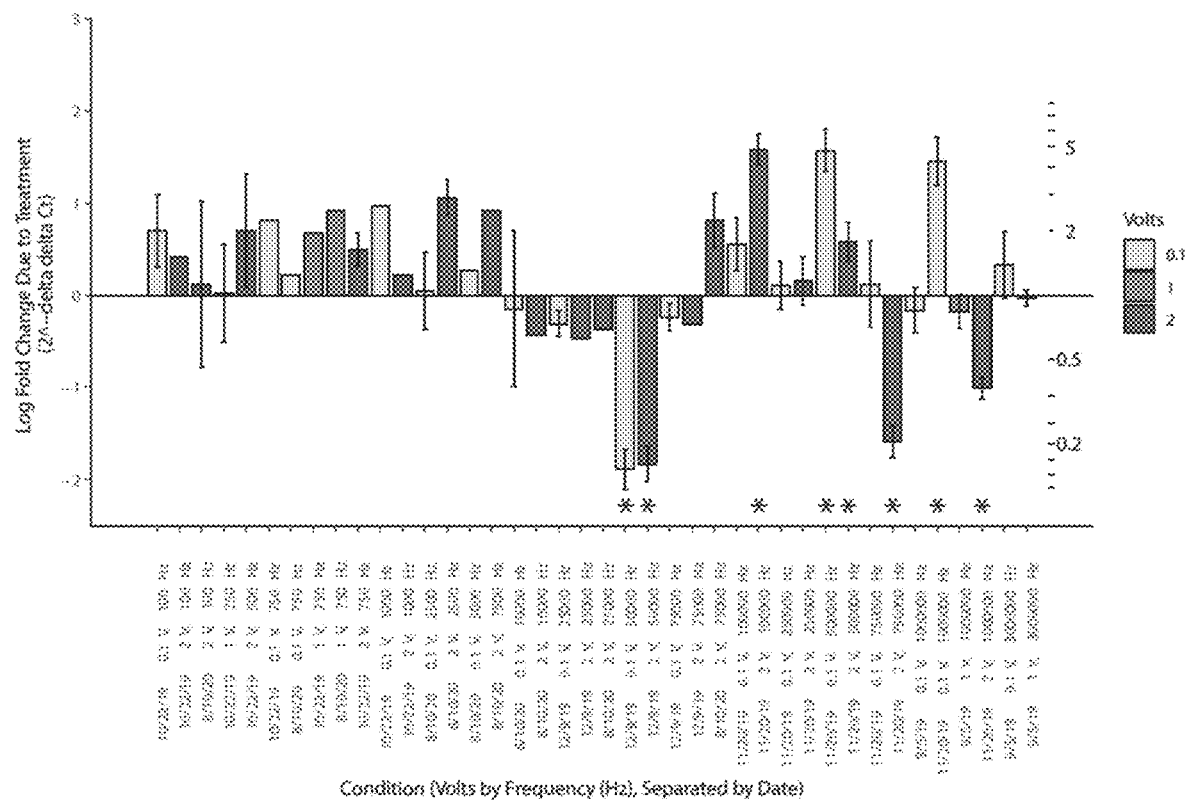
FIGS. 17-20 graphically depict the results of Example II.
Figure 18:
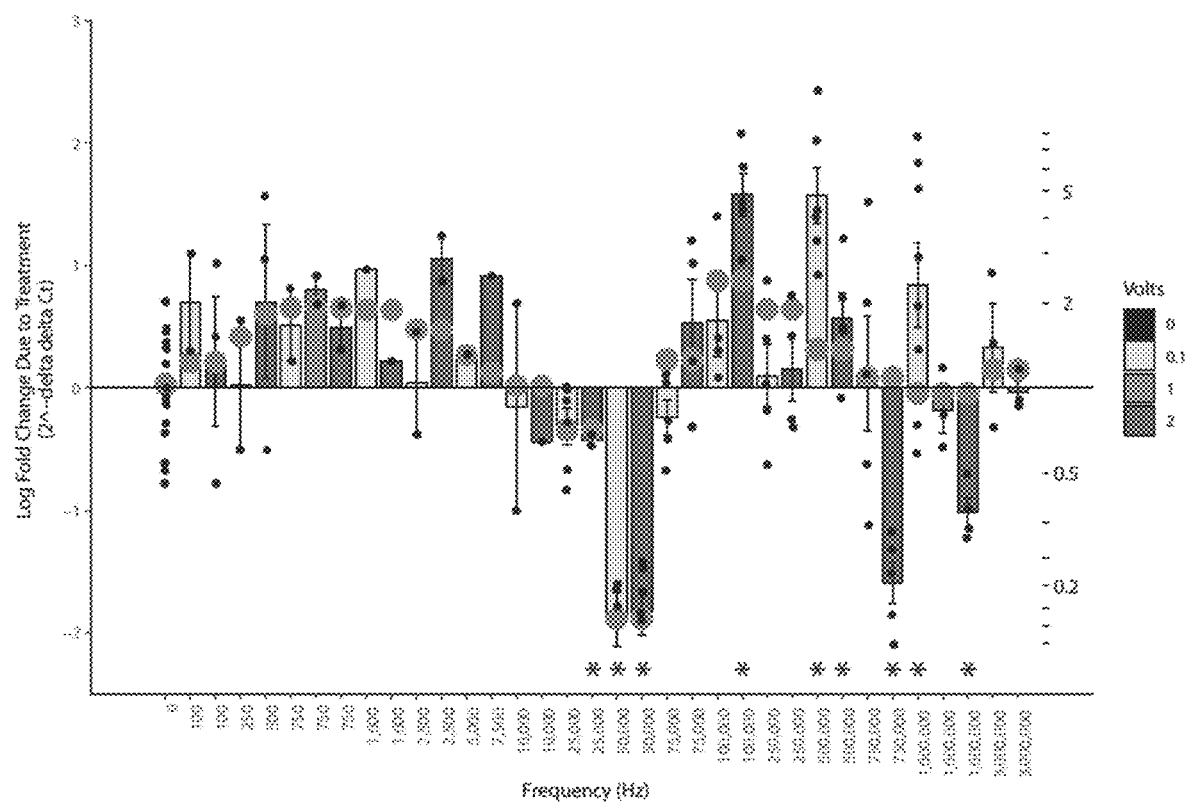
Figure 19:
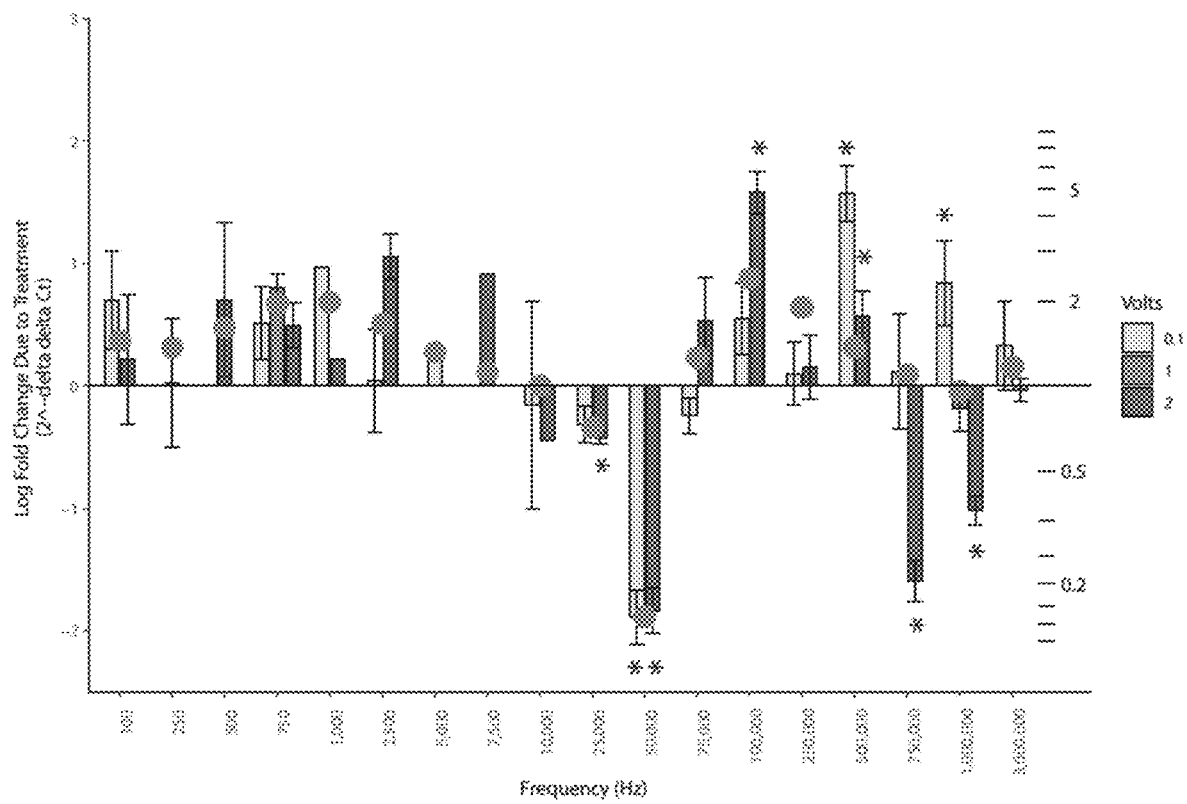
Figure 20:
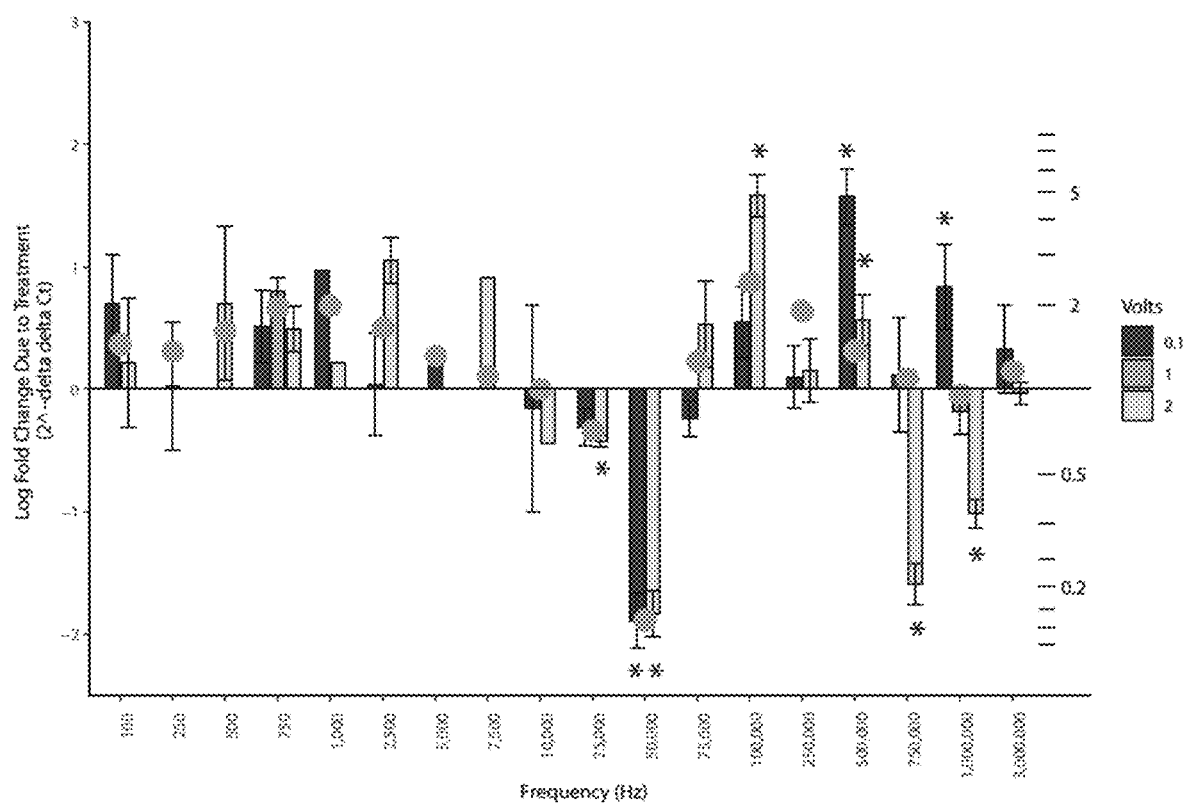

FIGS. 15 and 16 graphically depict the results of the experiment. Data in the graphs are Mean±SE.

Main effect of frequency was tested with an ANOVA (with frequency as continuous and categorical factor), Polynomial Model, and General Additive Model.

A repeated one-sample t-test was performed to test if the fold change due to treatment (2^-delta-delta Ct) was significant and were corrected using the Benjamini & Hochberg (1995) method.

Conclusions: There was a main effect of frequency for klotho for all methods used: ANOVA with frequency as numeric ($p<0.001$) and factor ($p=0.048$), polynomial model ($p<0.001$) and a general additive model ($p=0.008$).

After adjustments (22 tests), one-sample T-Test showed that klotho expression (log fold change due to treatment) was elevated above controls (0 Hz) for the following frequencies: 5 Hz, 25 Hz to 750 Hz, and 2,500 Hz.

Example III—Controlling Expression and/or Release of Klotho

Samples of cultured cells (e.g., osteoblasts) were stimulated for 30 minutes using a square, biphasic waveform at 50% duty (1 V at 5 Hz to 1 MHz). Bioelectric stimulation was applied to the cultured cells in vitro using a commercially available constant voltage waveform generator RIGOL LXI 1022Z (Beaverton, OR, US) via a 6-well stimulating plate interface (IONOPTIX, Westwood, MA, US).

FIGS. 17-20 graphically depict the results of the experiment. Data in graphs are Mean±SE.

qPCR triplicate measures with standard deviations above 1 were removed.

Normality of tests were evaluated using scatter plots.

Main effects of frequency and volts were tested with a Polynomial Model (8th for Frequency and 1st for Volts) and a Generalized Additive Model using Cubic B-Splines (df=11).

A one-sample T-Test was performed to test if the log fold change due to treatment (2^-delta-delta Ct) were significant.

Repeated T-Tests were corrected using the Benjamini & Hochberg (1995) method.

Frequency to the Polynomial of 8 fit was the best fit of the polynomial models tested for Klotho gene expression, adjusted $R^2=0.58$, $p<0.001$. The General Additive Model fit the data, but not better than the polynomial model, adjusted $R^2=0.36$, $p<0.001$. However, the General Additive Model provided the best explanation of the underlying biological theory for KLOTHO gene expression from electrical stimulations.

Voltage was not related to klotho gene expression.

After adjustments (29 tests), one-sample T-test showed that klotho expression was reduced for stimulations at 25,000 Hz, 50,000 Hz, and 750,000 Hz. Expression was increased for stimulations of 100,000 Hz and 500,000 Hz. Lastly, frequencies at and above 1,000,000 Hz had mixed results. A cut score at 100,000 Hz was identified between frequencies that decreased (lower than 100,000 Hz) and increased (at or above 100,000 Hz) klotho expression (Sensitivity: 0.86; specificity: 0.48; AUC 60%).

Example IV—Controlling Expression and/or Release of Klotho

The objective of this study was to analyze the gene expression of Klotho in C2C12 cells using RT-qPCR. Electrical Signals: The C2C12 cells were stimulated for 60 minutes, 300 μs continuous cycle using a Mettler™ stimulator at various frequencies and currents ranging from 0.5 mA, 2 mA, and 5 mA.

Methods: Bioelectric stimulation was applied to cells in vitro using a commercially available Mettler stimulator via a 6-well stimulating plate interface (IONOPTIX, Westwood, MA, USA). To induce uniform electric fields in all stimulation chambers, 1.3 mL of DMEM solution was added to each well before BES signal application.

Cells were plated in dishes and cultured to 80% to 100% confluency. Once confluent, cells were stimulated using an electrode array, which was inverted and introduced into the 6-well dish where cells were grown. Each well received uniform stimulation via a pair of carbon electrodes positioned at opposite sides.

Gene expression was determined by extracting mRNA according to the manufacturer's instructions. RNA quality was determined using a spectrophotometer and was reverse transcribed using a cDNA conversion kit. The cDNA and TaqMan Master Mix was used.

Figures 21, 22:
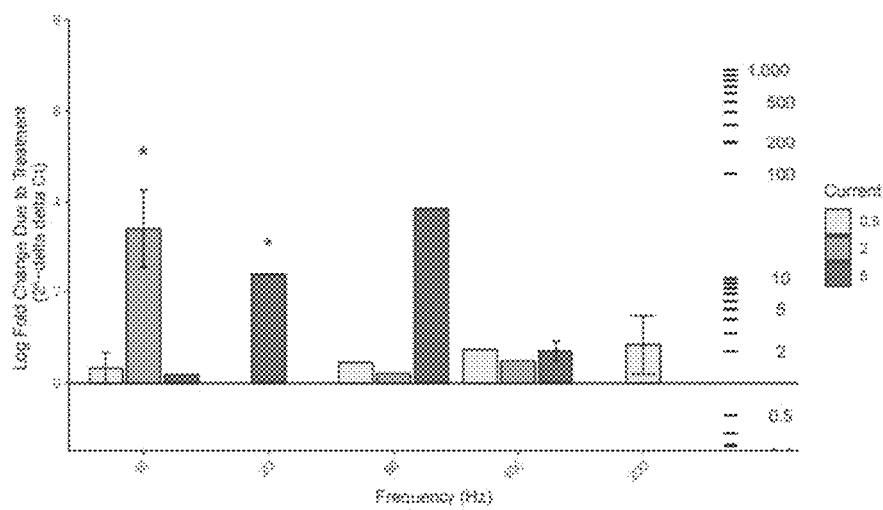
FIG. 21 graphically depicts klotho gene expression in C2C12 cells stimulated for 60 minutes as per Example III.
FIG. 22 is a table showing gene expression of C2C12 cells normalized to GAPDH using RT-qPCR as per Example III.

FIG. 21 graphically depicts klotho gene expression in C2C12 cells stimulated for 60 minutes. FIG. 22 is a table showing gene expression of C2C12 cells normalized to GAPDH using RT-qPCR.

The effects of C2C12 stimulated for 60 minutes at various frequencies and currents using a Mettler stimulator. After adjustments, a one-sample T-Test showed that klotho increased in the following conditions: 10 Hz at 2 mA, 20 Hz at 0.5 mA and 5 mA, and 50 Hz at 5 mA (which increased klotho 6088 fold). The ANOVA revealed Current influenced the magnitude of increase of klotho, likely meaning 0.5 mA had lower increases in klotho than 2 mA and 5 mA.

Example V—Kidney Treatment

A bioelectric stimulator is programmed to upregulate expression of Klotho (20 Hz for 30 minutes, 0.1 V (100 mV), and a 7.8 ms pulse duration minutes twice a week application) for treatment of a kidney patient. The bioelectric signal is applied to the thigh of the patient. Both the patient's muscles and the patient's kidneys have improved function.

Example VI—Further Kidney Treatment

In addition to being programmed to upregulate expression of Klotho, a preferred bioelectric stimulator for treating a subject's kidney(s) is programmed to produce bioelectric signals in the following order: 1. SDF-1 (see, e.g., FIGS. 11 and 12; a stem cell homing factor—recruits a person's own stem cells); 2. VEGF (see, e.g., FIG. 7; for new blood vessel growth); 3. IGF-1 (see, e.g., FIG. 6; for DNA repair at the level of the nucleus); 4. Follistatin (see, e.g., FIG. 5; for muscle and tissue regeneration); 5. RANKL (see, e.g., FIG. 8; for demineralization and tissue loosening when needed); 6. Hepatocyte Growth Factor (see, e.g., FIG. 9; tissue regeneration); 7. eNOS (for dilating blood vessels for increasing flow—e.g., using a bioelectric signal includes (within 15%): alternating high-frequency (HF) and medium-frequency signals (MF), symmetric, biphasic, trapezoid pulses, with 400-μs pulse duration and 1.5/1-s ramp-up/ramp-down duration, respectively). 8. Tropoelastin (see, e.g., FIG. 13; increases elasticity of any tissues such as skin, arteries, aorta, heart and promotes healing of wounds); 9. Activin A+B (see, e.g., FIG. 10); and 10. EGF (for regeneration, using, e.g., 10 V/cm (5 V here), 500 Hz, pulse width 180 s, square wave). These bioelectric signals are applied subsequent to the Klotho bioelectric signals.

Example VII—Kidney Treatment

In addition to being programmed to upregulate expression of Klotho, a preferred bioelectric stimulator for treating a subject's kidney(s) is programmed to produce bioelectric signal PDGF. A bioelectric signal for platelet-derived growth factor ("PDGF") is (within 15%) 3 V/cm, 10 Hz, 2 μA, and pulse duration of 0.2 ms. Another bioelectric signal for PDGF is (within 15%) 20 V/cm, 100 Hz, 0.25 mA (2.5e-7 amps), and pulse duration of 40 pulses/s, width of 100 s. Another bioelectric signal for PDGF is (within 15%) 20 V for 1 minute, 20 mV for 10 minutes, current of 0.25 mA, pulse duration of 40 pulses/s, pulse width of 100 μs, and frequency of 100 Hz for 5 minutes followed by 528 Hz for 3 minutes and 432 Hz for 3 minutes and 50 Hz for 3 minutes. These bioelectric signals are applied to the subject subsequent to the Klotho bioelectric signals.

Example VIII—Erectile Dysfunction

A bioelectric stimulator is first programmed to upregulate expression of Klotho (20 Hz for 30 minutes (e.g., 15 minutes twice a day), 0.1 V (100 mV), and a 7.8 ms pulse duration minutes twice a week application). The bioelectric stimulator is further programmed to produce a bioelectric signal appropriate for upregulating expression of IGF-1 (e.g., 3 mV with electric frequency of 22 Hz, and current of 1 mA for 15 minutes and 3 mA for 15 minutes.) The bioelectric stimulator is further programmed to upregulate expression of follistatin (e.g., a bioelectric signal of 10 V at 50 Hz and 100 Hz, 0.25 mA for one (1) minute.)

This regime is applied to a male subject in the groin area to prevent and/or treat erectile dysfunction.

Example IX—Hair Loss

A bioelectric stimulator is programmed to produce bioelectric signals that upregulate expression of HGF, IGF-1, PDGF and Klotho (see, e.g., the incorporated U.S. Pat. No. 10,960,206 to Leonhardt et al. (Mar. 30, 2021) for "Bioelectric Stimulator" for exemplary bioelectric signals). A bioelectric signal for hepatocyte growth factor ("HGF") is (within 15%) 3.5 V stimulation in 10 second bursts, 1 burst every 30 seconds at a frequency of about 50 Hz (duration 5 minutes) (wherein the electrical signal is as measured three (3) mm deep into the tissue). A bioelectric signal for Insulin-like growth factor 1 (IGF-1) is (within 15%) 3 mV with a frequency of about 22 Hz, and a current of about 1 mA, followed by 3 mA. A bioelectric signal for platelet-derived growth factor ("PDGF") is (within 15%) 3 V/cm, 10 Hz, 2 μA, and pulse duration of 0.2 ms. Another bioelectric signal for PDGF is (within 15%) 20 V/cm, 100 Hz, 0.25 mA (2.5e-7 amps), and pulse duration of 40 pulses/s, width of 100 s. Another bioelectric signal for PDGF is (within 15%) 20 V for 1 minute, 20 mV for 10 minutes, current of 0.25 mA, pulse duration of 40 pulses/s, pulse width of 100 s, and frequency of 100 Hz for 5 minutes followed by 528 Hz for 3 minutes and 432 Hz for 3 minutes and 50 Hz for 3 minutes. A bioelectric signal for Klotho is a biphasic pulse at (within 15%) 20 Hz, 0.1 V, and a 7.8 ms pulse duration.

The bioelectric stimulator is connected to a subject's scalp (for example, via electrodes), where the subject is suffering from hair thinning and/or baldness. A bioelectric signal regimen is applied to the subject's scalp. Increased hair growth is experienced by the subject.

LED light signaling sequences may also be applied to the subject's scalp. See, e.g., Joo, Hong Jin et al. "Various Wavelengths of Light-Emitting Diode Light Regulate the Proliferation of Human Dermal Papilla Cells and Hair Follicles via Wnt/β-Catenin and the Extracellular Signal-Regulated Kinase Pathways," *Annals of Dermatology* vol. 29, 6 (2017): 747-754. doi:10.5021/ad.2017.29.6.747, and Kim et al. "Wnt/β-catenin and ERK pathway activation: A possible mechanism of photobiomodulation therapy with light-emitting diodes that regulate the proliferation of human outer root sheath cells," *Lasers Surg. Med.* 2017 December; 49(10):940-947. doi: 10.1002/lsm.22736. Epub 2017 Sep. 25. PMID: 28944964.

Treatment of the subject may also be supplemented with the administration of *Polygonum multiflorum* Radix (PMR). See, e.g., Li, Yunfei et al. "Hair Growth Promotion Activity and Its Mechanism of *Polygonum multiflorum*," *Evidence-Based Complementary And Alternative Medicine: eCAM* vol. 2015 (2015): 517901. doi:10.1155/2015/517901.

The subject may also be administered adipose-derived stem cells. Fukuoka et al. "Hair Regeneration Therapy: Application of Adipose-Derived Stem Cells," *Current Stem Cell Research & Therapy* vol. 12, 7 (2017): 531-534. doi:10.2174/1574888X12666170522114307.

Example X—Diabetic Neuropathy

A bioelectric signal of 20 Hz was applied to 10 subjects patients (5 treated and 5 controls) included in a clinical study. As the means and SD show, an overexpression for Klotho protein (168%) is observed in the treated group over 4 and 8 weeks. The values for creatinine until the present moment did not change between groups.

|  | Control (n = 5) | | | BES (n = 5) | | |
| --- | --- | --- | --- | --- | --- | --- |
|  | Baseline | 4 weeks | 8 weeks | Baseline | 4 weeks | 8 weeks |
| Klotho | 137.5 ± 50.1 | 139.2 ± 53.8 | 135.4 ± 34.7 | 145.7 ± 39.6 | 205.1 ± 75.4 | 227.7 ± 98.3 |
| Creatinine | 7.3 ± 1.8 | 7.2 ± 1.3 | 7.8 ± 2.4 | 9.2 ± 2.7 | 10.1 ± 2.0 | 9.6 ± 2.3 |

References: Lee et al. "Klotho ameliorates diabetic nephropathy via LKB1-AMPK-PGC1α-mediated renal mitochondrial protection," *Biochemical and Biophysical Research Communications* Volume 534, 1 Jan. 2021, Pages 1040-1046; and Hu, Ming Chang et al. "Renal and extrarenal actions of Klotho," *Seminars In Nephrology* vol. 33, 2 (2013): 118-29. doi:10.1016/j.semnephrol.2012.12.013.

REFERENCES (The contents of the entirety of each of which is incorporated herein by this reference.)

Apel, P J. J. Ma, M, Callahan, C. N. Northam, T. B. Alto, W, E, Sonntag, and Z Li (2010), Effect of locally delivered IGF-1 on nerve regeneration during aging: an experimental study in rats, *Muscle & nerve,* 4(3), 335-341. doi.org/10.1002/mus.21485.

Ayden et al. "Focusing of electromagnetic waves by a left-handed metamaterial flat lens," *Optics Express* (31 Oct. 2005) 13(22):8753-8759.

Bourdillon et al. "Electromagnetic Brain Stimulation in Patients With Disorders of Consciousness," *Front. Neurosci.* (18 Mar. 2019): doi.org/10.3389/fnins.2019.00223.

Bäck et al. "Endogenous Calcification Inhibitors in the Prevention of Vascular Calcification: A Consensus Statement From the COST Action EuroSoftCalcNet," *Front. Cardiovasc. Med.,* 918 January 2019): doi.org/10.3389/fcvm.2018.00196.

Bre et al. "Prevention of bioprosthetic heart valve calcification: strategies and outcomes," *Curr. Med Chem.* 2014; 21(22):2553-64. doi: 10.2174/09298673216661312151216. PMID: 24358975.

Brüggemann A. K., "Effects of Neuromuscular Electrical Stimulation During Hemodialysis on Peripheral Muscle Strength and Exercise Capacity: A Randomized Clinical Trial," *Arch. Phys. Med Rehabil.* 2017 May; 98(5):822-831.e1. doi: 10.1016/j.apmr.2016.12.009. Epub 2017 Jan. 16.

Caradu et al. "Endogenous Sonic Hedgehog limits inflammation and angiogenesis in the ischaemic skeletal muscle of mice," *Cardiovasc. Res.* 2018 Apr. 1; 114(5):759-770. doi: 10.1093/cvr/cvy017. PMID: 29365079.

Carboni et al. "An initial study on the effect of functional electrical stimulation in erectile dysfunction: a randomized controlled trial." *Int. J. Impot. Res.* 2018 June; 30(3):97-101. doi: 10.1038/s41443-018-0024-8. Epub 2018 May 22. PMID: 29785045.

Chen et al. "Deficiency in the anti-aging gene Klotho promotes aortic valve fibrosis through AMPKα-mediated activation of RUNX2," *Aging Cell* vol. 15, 5 (2016): 853-60. doi:10.1111/acel.12494.

Chen, Tianlei et al. "The Role and Mechanism of α-Klotho in the Calcification of Rat Aortic Vascular Smooth Muscle Cells," *BioMed Research International* vol. 2015 (2015): 194362. doi:10.1155/2015/194362.

Chen, Nai-Ching et al. "The Strategy to Prevent and Regress the Vascular Calcification in Dialysis Patients," *BioMed Research International,* vol. 2017, Article ID 9035193, 11 pages, 2017; doi.org/10.1155/2017/9035193.

Cheng, Xi et al. "The Role of SDF-1/CXCR4/CXCR7 in Neuronal Regeneration after Cerebral Ischemia," *Frontiers in Neuroscience* vol. 11 590. 24 Oct. 2017, doi: 10.3389/fnins.2017.00590.

Chera et al. "Diabetes recovery by age-dependent conversion of pancreatic δ-cells into insulin producers," *Nature,* 2014; DOI: 10.1038/nature13633.

Chu et al. "Mechanical stretch induces hair regeneration through the alternative activation of macrophages," *Nature Communications,* 10(1), 1524 (2019). doi.org/10.1038/s41467-019-09402-8.

Columbia "Implant Procedure Concepts—Pacemaker, ICD and CRT Overview," columbia.edu/itc/hs/medical/hickey/docs/Pacemaker,%20ICD %20and %20CRT %20Overview %200 22007.pdf Prochazka et al., "Cocktail of Factors from Fat-derived Stem Cells Shows Promise for Critical Limb Ischemia," www.sciencenewsline.com/news/2016012204520017.html (Jan. 21, 2016).

Deng et al. "Effects of SDF-1/CXCR4 on the Repair of Traumatic Brain Injury in Rats by Mediating Bone Marrow Derived Mesenchymal Stem Cells," *Cell Mol. Neurobiol.* 2018 March; 38(2):467-477. doi: 10.1007/s10571-017-0490-4. Epub 2017 May 8. Erratum in: *Cell Mol. Neurobiol.* 2021 April; 41(3):617-618. PMID: 28484859.

Di Iorio et al., "High-frequency external muscle stimulation in acute kidney injury (AKI): potential shortening of its clinical course," *Clin. Nephrol.* 2013 January; 79 Suppl. 1:S37-45.

Diaco et al. "Amniotic fluid-derived stem cells as an effective cell source for transplantation therapy in stroke," *Brain Circ.* 2015; 1:119-24.

Dote-Montero et al. "Predictors of Sexual Desire and Sexual Function in Sedentary Middle-Aged Adults: The Role of Lean Mass Index and S-Klotho Plasma Levels. The FIT-AGEING Study," *J. Sex Med* 2020 April; 17(4):665-677. doi: 10.1016/j.jsxm.2020.01.016. Epub 2020 Feb. 20. PMID: 32089483.

Fukuoka et al. "Hair Regeneration Therapy: Application of Adipose-Derived Stem Cells," *Current Stem Cell Research & Therapy* vol. 12, 7 (2017): 531-534. doi: 10.2174/1574888X12666170522114307.

Geribaldi-Doldin et al. "Protein Kinase C: Targets to Regenerate Brain Injuries?" *Front. CellDev. Biol.,* 20 Mar. 2019): doi.org/10.3389/fcell.2019.00039.

Ghuman et al. "Biodegradation of ECM hydrogel promotes endogenous brain tissue restoration in a rat model of stroke," *Acta Biomater* 2018 Oct. 15; 80:66-84. doi: 10.1016/j.actbio.2018.09.020. Epub 2018 Sep. 16. PMID: 30232030; PMCID: PMC6217851.

Guyot et al. "Pancreatic nerve electrostimulation inhibits recent-onset autoimmune diabetes," *Nat. Biotechnol.* 37, 1446-1451 (2019): doi.org/10.1038/s41587-019-0295-8.

Hopkins Medicine, "Overview of Pacemakers and Implantable Cardioverter Defibrillators (ICDs)," hopkinsmedicine.org/healthlibrary/conditions/cardiovascular_diseases/overview of_pacemakers_and_implantable_cardioverter_defibrillators_icds_85,P00234/.

Hoyer et al. "Electroconvulsive therapy enhances the anti-ageing hormone Klotho in the cerebrospinal fluid of geriatric patients with major depression," *Eur. Neuropsychopharmacol.* 2018 March; 28(3):428-435. doi: 10.1016/j.euroneuro.2017.12.012. Epub 2017 Dec. 20. PMID: 29274997.

Hu, Ming Chang et al. "Renal and extrarenal actions of Klotho," *Seminars In Nephrology* vol. 33, 2 (2013): 118-29. doi:10.1016/j.semnephrol.2012.12.013.

Jayaraj et al. "Neuroinflammation: friend and foe for ischemic stroke," *J. Neuroinflammation* 16, 142 (2019): doi.org/10.1186/s12974-019-1516-2.

Joo, Hong Jin et al. "Various Wavelengths of Light-Emitting Diode Light Regulate the Proliferation of Human Dermal Papilla Cells and Hair Follicles via Wnt/β-Catenin and the Extracellular Signal-Regulated Kinase Pathways," *Annals of Dermatology* vol. 29, 6 (2017): 747-754. doi:10.5021/ad.2017.29.6.747.

Kim et al. "Wnt/β-catenin and ERK pathway activation: A possible mechanism of photobiomodulation therapy with light-emitting diodes that regulate the proliferation of human outer root sheath cells," *Lasers Surg. Med.* 2017 December; 49(10):940-947. doi: 10.1002/lsm.22736. Epub 2017 Sep. 25. PMID: 28944964.

Kinney B M, Lozanova P. "High intensity focused electromagnetic therapy evaluated by magnetic resonance imaging: Safety and efficacy study of a dual tissue effect based non-invasive abdominal body shaping," *Lasers Surg. Med* 2019 January; 51(1):40-46. doi: 10.1002/lsm.23024. Epub 2018 Oct. 10. PMID: 30302767; PMCID: PMC6585690.

Lang et al. "Therapeutic Interference with Vascular Calcification—Lessons From Klotho-Hypomorphic Mice and Beyond," *Front. Endocrinol.* (May 2018): doi.org/10.3389/fendo.2018.00207.

Lee et al. "Klotho ameliorates diabetic nephropathy via LKB1-AMPK-PGC1α-mediated renal mitochondrial protection," *Biochemical and Biophysical Research Communications* Volume 534, 1 Jan. 2021, Pages 1040-1046.

Lei, Yang et al. "Efficacy of reversal of aortic calcification by chelating agents," *Calcified Tissue International* Vol. 93, 5 (2013): 426-35. doi:10.1007/s00223-013-9780-0.

Lei, Yang "Mechanisms and Reversal Of Elastin Specific Medial Arterial Calcification" (2014). All Dissertations. 1307; tigerprints.clemson.edu/all_dissertations/1307/.

Leibrock et al. "You have access NH4C1 Treatment Prevents Tissue Calcification in Klotho Deficiency," *Journal of the American Society of Nephrology*, October 2015, 26 (10) 2423-2433.

Leon et al. "Peripheral Elevation of a Klotho Fragment Enhances Brain Function and Resilience in Young, Aging, and α-Synuclein Transgenic Mice," *Cell Reports* Volume 20, Issue 6, 6 Aug. 2017, Pages 1360-1371.

Li et al. "Hair Growth Promotion Activity and Its Mechanism of *Polygonum multiflorum,*" *Evid Based Complement. Alternat. Med* 2015; 2015:517901. doi: 10.1155/2015/517901. Epub 2015 Jul. 30. PMID: 26294926; PMCID: PMC4534627.

Li et al. "GDF10 is a signal for axonal sprouting and functional recovery after stroke," *Nat. Neurosci.* 2015; Epub 2015 Oct. 15.

Lim, Kenneth et al. "α-Klotho Expression in Human Tissues," *The Journal Of Clinical Endocrinology And Metabolism* vol. 100, 10 (2015): E1308-18. doi:10.1210/jc.2015-1800.

Lim et al. "Klotho: A Major Shareholder in Vascular Aging Enterprises," *Int. J. Mol. Sci.* 2019, 20(18), 4637; doi.org/10.3390/ijms20184637.

Liu, N., Matsumura et al. "Stem cell competition orchestrates skin homeostasis and ageing," *Nature* 568, 344-350 (2019); doi.org/10.1038/s41586-019-1085-7.

Malyshevskaya et al. "Role of Electrical Activity in Horizontal Axon Growth in the Developing Cortex: A Time-Lapse Study Using Optogenetic Stimulation," *PLOS ONE* (2013): doi.org/10.1371/journal.pone.0082954.

Martín-Núñez et al. "Implications of Klotho in vascular health and disease," *World J. Cardiol.* Dec. 26, 2014; 6(12): 1262-1269.

Martín-González et al. "Soluble α-Klotho in Liver Cirrhosis and Alcoholism, Alcohol and Alcoholism," Volume 54, Issue 3, May 2019, Pages 204-208.

Martinez-Redondo et al. "αKLOTHO and sTGFβR2 treatment counteract the osteoarthritic phenotype developed in a rat model," *Protein Cell.* 11, 219-226 (2020): doi.org/10.1007/s13238-019-00685-7.

Mir et al. "IGF-1 mediated Neurogenesis Involves a Novel RIT1/Akt/Sox2 Cascade," *Sci. Rep.* 7, 3283 (2017): doi.org/10.1038/s41598-017-03641-9.

Missoum et al. "Recent Updates on Mesenchymal Stem Cell Based Therapy for Acute Renal Failure," *Curr. Urol.* 2019; 13:189-199; DOI: 10.1159/000499272.

Morales-Garcia et al. "The alkaloids of Banisteriopsis caapi, the plant source of the Amazonian hallucinogen Ayahuasca, stimulate adult neurogenesis in vitro," *Sci. Rep.* 7, 5309 (2017): doi.org/10.1038/s41598-017-05407-9.

Nakamura et al. "Eicosapentaenoic acid prevents arterial calcification in klotho mutant mice," *PLoS One.* 2017 Aug. 3; 12(8):e0181009. doi: 10.1371/journal.pone.0181009. PMID: 28771600; PMCID: PMC5542469.

Nih et al. "Dual-function injectable angiogenic biomaterial for the repair of brain tissue following stroke," *Nature Mater.* 17, 642-651 (2018): doi.org/10.1038/s41563-018-0083-8.

Nowak et al. "Prognostic Value and Link to Atrial Fibrillation of Soluble Klotho and FGF23 in Hemodialysis Patients," *PLoS One.* 2014 Jul. 3; 9(7):e100688. doi: 10.1371/journal.pone.0100688.

O'Neill, W Charles, and Koba A Lomashvili. "Recent progress in the treatment of vascular calcification," *Kidney International* vol. 78, 12 (2010): 1232-9. doi:10.1038/ki.2010.334.

Pai et al. "Endogenous Gradients of Resting Potential Instructively Pattern Embryonic Neural Tissue via Notch Signaling and Regulation of Proliferation," *Journal of Neuroscience*, 2015; 35 (10): 4366 DOI: 10.1523/JNEUROSCI.1877-14.2015.

Papaioannou et al. "Sonic Hedgehog signaling limits atopic dermatitis via Gli2-driven immune regulation," *J. Clin. Invest.* 2019; 129(8):3153-3170; doi.org/10.1172/JCI125170.

Paroni et al. "Klotho Gene and Selective Serotonin Reuptake Inhibitors: Response to Treatment in Late-Life Major Depressive Disorder," *Mol. Neurobiol.* 2017 March; 54(2):1340-1351. doi: 10.1007/s12035-016-9711-y. Epub 2016 Feb. 3. PMID: 26843110.

Prather et al. "Longevity factor klotho and chronic psychological stress," *Translational Psychiatry,* 2015; 5 (6): e585 DOI: 10.1038/tp.2015.81.

Prud'homme et al. "The anti-aging protein Klotho is induced by GABA therapy and exerts protective and stimulatory effects on pancreatic beta cells," *Biochem. Biophys. Res. Commun.* 2017 Dec. 2; 493(4):1542-1547. doi: 10.1016/j.bbrc.2017.10.029. Epub 2017 Oct. 6. PMID: 28993191.

Qi et al. "Enhancement of neural stem cell survival, proliferation and differentiation by IGF-1 delivery in graphene oxide-incorporated PLGA electrospun nanofibrous mats," *RSC Adv.,* 2019, 9, 8315-8325.

Rhee et al. "Neural stem cells secrete factors facilitating brain regeneration upon constitutive Raf-Erk activation," *Sci. Rep.* 6, 32025 (2016): doi.org/10.1038/srep32025.

Salcedo et al., "Low current electrical stimulation upregulates cytokine expression in the anal sphincter," *Int. J. Colorectal Dis.,* 2012 February; 27(2):221-5. doi: 10.1007/s00384-011-1324-3. Epub (October 2011).

Sachdeva et al. "Klotho and the Treatment of Human Malignancies," *Cancers* 2020, 12, 1665; doi:10.3390/cancers12061665.

Sadagurski, Marianna et al. "Insulin-like growth factor 1 receptor signaling regulates skin development and inhibits skin keratinocyte differentiation," *Molecular and Cellular Biology* vol. 26, 7 (2006): 2675-87. doi:10.1128/MCB.26.7.2675-2687.2006.

Savastano et al. "Insulin-like Growth Factor-1, Psoriasis, and Inflammation: A Ménage à Trois?" *European Journal of Inflammation* Volume: 9 issue: 3, page(s): 277-283 (2011).

Sharma et al. "Insulin demand regulates β cell number via the unfolded protein response," *Journal of Clinical Investigation*, 2015; DOI: 10.1172/JCI79264.

Schardong et al. (2017), "Effects of Intradialytic Neuromuscular Electrical Stimulation on Strength and Muscle Architecture in Patients with Chronic Kidney Failure: Randomized Clinical Trial," *Artif Organs*. 2017 November; 41(11):1049-1058. doi: 10.1111/aor.12886. Epub 2017 Jun. 16.

Schardong et al. (2018), "Intradialytic neuromuscular electrical stimulation reduces DNA damage in chronic kidney failure patients: a randomized controlled trial," *Biomarkers*, 23:5, 495-501, DOI: 10.1080/1354750X.2018.1452049.

Sieg, F. "Mini-review of neural regeneration peptides in brain development," *Journal of Stem Cell Research & Therapeutics* 1 (2016): DOI: 10.15406/JSRT.2016.01.00025 Corpus ID: 14566389.

Sood et al. "Fetal Brain Extracellular Matrix Boosts Neuronal Network Formation in 3D Bioengineered Model of Cortical Brain Tissue," *ACS Biomater. Sci. Eng.* 2016, 2, 1, 131-140.

Stief et al., "Functional electromyostimulation of the corpus cavernosum penis—preliminary results of a novel therapeutic option for erectile dysfunction," *World J. Urol.* (1995) 13:243-247.

Sun, Huidong et al. "Overexpression of Klotho suppresses liver cancer progression and induces cell apoptosis by negatively regulating wnt/β-catenin signaling pathway," *World Journal of Surgical Oncology* vol. 13 307. 24 Oct. 2015, doi:10.1186/s12957-015-0717-0.

Takenaka et al., "Klotho protein supplementation reduces blood pressure and renal hypertrophy in db/db mice, a model of type 2 diabetes," *Acta. Physiol. (Oxf.)* 2019 February; 225(2):e13190. doi: 10.1111/apha.13190. Epub 2018 Oct. 16.

Tang-Schomer M D. "3D axon growth by exogenous electrical stimulus and soluble factors," *Brain Res*. 2018 Jan. 1; 1678:288-296. doi: 10.1016/j.brainres.2017.10.032. Epub 2017 Oct. 31. PMID: 29097106.

The et al. "Mechanistic Roles of Matrilin-2 and Klotho in Modulating the Inflammatory Activity of Human Aortic Valve Cells," *Cells* 2020, 9, 385; doi:10.3390/cells9020385.

Thurston et al. "Tumor necrosis factor and interferon-gamma down-regulate Klotho in mice with colitis," *Gastroenterology*. 2010 April; 138(4):1384-94, 1394.e1-2. doi: 10.1053/j.gastro.2009.12.002. Epub 2009 Dec. 11. PMID: 20004202; PMCID: PMC3454518.

Torbus-Paluszczak et al., "Klotho protein in neurodegenerative disorders," *Neurol. Sci.* 39, 1677-1682 (2018): doi.org/10.1007/s10072-018-3496-x.

van Kampen et al., "Treatment of Erectile Dysfunction by Perineal Exercise, Electromyographic Biofeedback, and Electrical Stimulation," *Phys. Ther.* 2003; 83(6):536-543.

Wang, Na et al. "Secreted klotho from exosomes alleviates inflammation and apoptosis in acute pancreatitis," *American Journal Of Translational Research* vol. 11, 6 3375-3383. 15 Jun. 2019.

Witkowski et al. "Klotho—a Common Link in Physiological and Rheumatoid Arthritis-Related Aging of Human CD4+ Lymphocytes," *J. Immunol*. (2007), 178(2):771-777; DOI: doi.org/10.4049/jimmunol.178.2.771.

Xia, Weiwei et al. "Klotho Contributes to Pravastatin Effect on Suppressing IL-6 Production in Endothelial Cells," *Mediators of Inflammation* vol. 2016 (2016): 2193210. doi:10.1155/2016/2193210.

Xie et al. "Klotho Acts as a Tumor Suppressor in Cancers," July 2013 *Pathology & Oncology Research* 19(4) DOI: 10.1007/s12253-013-9663-8.

Xuan, Nguyen Thi, and Nong Van Hai. "Changes in expression of klotho affect physiological processes, diseases, and cancer," *Iranian journal of basic medical sciences* vol. 21, 1 (2018): 3-8.

Yaden et al., "Follistatin: a novel therapeutic for the improvement of muscle regeneration," *Journal of Pharmacology and Experimental Therapeutics* Mar. 13, 2014, jpet.113.211169; DOI: doi.org/10.1124/jpet.113.211169.

Yamauchi et al. "Wound healing delays in α-Klotho-deficient mice that have skin appearance similar to that in aged humans—Study of delayed wound healing mechanism," *Biochemical and Biophysical Research Communications* Volume 473, Issue 4, 13 May 2016, Pages 845-852.

Yan Cai et al. "Intermedin inhibits vascular calcification by increasing the level of matrix γ-carboxyglutamic acid protein," *Cardiovascular Research*, Volume 85, Issue 4, 1 Mar. 2010, Pages 864-873, doi.org/10.1093/cvr/cvp366.

Yarbrough et al. "Specific binding and mineralization of calcified surfaces by small peptides," *Calcified Tissue International* Vol. 86, 1 (2010): 58-66. doi:10.1007/s00223-009-9312-0.

Zhang, Beibei et al. "Klotho Protein Protects Human Keratinocytes from UVB-Induced Damage Possibly by Reducing Expression and Nuclear Translocation of NF-κB," *Medical Science Monitor: International Medical Journal of Experimental and Clinical Research* vol. 24 8583-8591. 27 Nov. 2018, doi:10.12659/MSM.910687.

Zhang W G et al. "Association of Klotho and interleukin 6 gene polymorphisms with aging in Han Chinese population," *J. Nutr. Health Aging*. 2014 December; 18(10):900-4. doi: 10.1007/s12603-014-0470-z. PMID: 25470806.

Zhao and Willing "Enhancing endogenous capacity to repair a stroke-damaged brain: An evolving field for stroke research," *Progress in Neurobiology* Volumes 163-164, April-May 2018, Pages 5-26.

Zhou et al. "Advance of Stem Cell Treatment for Traumatic Brain Injury," *Front. Cell. Neurosci.*, (13 Aug. 2019): doi.org/10.3389/fncel.2019.00301.

Zhu et al. "Klotho controls the brain-immune system interface in the choroid plexus," *PNAS* Nov. 27, 2018 115 (48) E11388-E11396; first published Nov. 9, 2018.

US Patent Application Publication 20190125932A1 to Leonhardt & Donofrio (May 2, 2019) for "Preventing blood clot formation, calcification and/or plaque formation on blood contact surface(s)."

US Patent Application Publication 20190290541 to Greiner et al. (Sep. 26, 2019) for "Implantable Electroacupuncture System and Method for Treating Depression and Similar Mental Conditions."

US Patent Application Publication US 20200324106 A1 to Leonhardt et al. (Oct. 15, 2020) for "Bioelectric Stimulation for Sonic Hedgehog Expression."

US Patent Application Publication US 20210228870 A1 to Leonhardt et al. (Jul. 29, 2021) for "COL17A1 Modulation."

U.S. Pat. No. 4,976,733 to Giradot (Dec. 11, 1990) for "Prevention of prosthesis calcification."

U.S. Pat. No. 9,987,326 to Koeffler et al. (Jun. 5, 2018) for "Klotho protein and related compounds for the treatment and diagnosis of cancer."

U.S. Pat. No. 10,646,644 to Leonhardt et al. (May 12, 2020)) for "Stimulator, Pump & Composition."

U.S. Pat. No. 10,960,206 to Leonhardt et al. (Mar. 30, 2021) for "Bioelectric Stimulator."

U.S. Pat. No. 11,110,274 to Leonhardt (Sep. 7, 2021)) for "System and Method for Treating Inflammation."

WO 2016135295 A1 to Gunther et al. (Sep. 1, 2016) for "Genetically modified mesenchymal stem cell expressing klotho."

What is claimed is:

1. A method of treating a cell, the method comprising:
stimulating the cell to express and/or release Klotho polypeptide by applying a bioelectric signal to the cell, wherein the bioelectric signal has a square, biphasic waveform at 50% duty and a frequency selected from the group consisting of 5 Hz, 10 Hz, 20 Hz, 25 Hz, 50 Hz, 75 Hz, 100 Hz, 250 Hz, 500 Hz, 750 Hz, 2,500 Hz, 100,000 Hz, 500,000 Hz, and 1 MHz.

2. The method according to claim 1, wherein the cell is comprised within a subject.

3. The method according to claim 1, wherein the bioelectric signal has a frequency of 5 Hz.

4. The method according to claim 1, wherein the bioelectric signal has a frequency of 20 Hz.

5. The method according to claim 1, wherein the bioelectric signal has a frequency of 25 Hz.

6. The method according to claim 1, wherein the bioelectric signal has a frequency of 50 Hz.

7. The method according to claim 1, wherein the bioelectric signal has a frequency of 100 Hz.

8. The method according to claim 1, wherein the bioelectric signal has a frequency of 500 Hz.

9. The method according to claim 1, wherein the bioelectric signal has a frequency of 750 Hz.

10. A method of using a bioelectric stimulator programmed to produce one or more bioelectric signals for stimulation of cellular tissue, wherein at least one such bioelectric signal upregulates expression of Klotho by the cellular tissue, the method comprising:
applying the bioelectric stimulator to target tissue of a subject, and
actuating the bioelectric stimulator to produce the one or more programmed bioelectric signals,
wherein the bioelectric stimulator is programmed with at least one bioelectric signal having a square, biphasic waveform at 50% duty and a frequency selected from the group consisting of 5 Hz, 10 Hz, 20 Hz, 25 Hz, 50 Hz, 75 Hz, 100 Hz, 250 Hz, 500 Hz, 750 Hz, 2,500 Hz, 100,000 Hz, 500,000 Hz, and 1 MHz.

11. The method according to claim 10, wherein the target tissue is selected from the group consisting of muscle, brain, kidney, pancreas, bone, tumor, and nerve.

12. The method according to claim 10, wherein the subject has been diagnosed as having a condition selected from the group consisting of cancer, a tumor, atrial fibrillation, aortic valve calcification, arterial calcification, tissue calcification, erectile dysfunction, hair loss, and calcification of the breast.

13. The method according to claim 10, wherein the subject is receiving or has received radiation treatment or chemotherapy for cancer.

14. The method according to claim 10, wherein the amount of circulating Klotho in the subject's blood stream is increased by at least 200% over normal by applying the bioelectric stimulator to the target tissue and actuating the bioelectric stimulator to produce the one or more programmed bioelectric signals.

15. The method according to claim 14, wherein the subject's risk of cancer is thereby reduced by applying the bioelectric stimulator to the target tissue and actuating the bioelectric stimulator to produce the one or more programmed bioelectric signals.

16. The method according to claim 10, wherein the bioelectric signal is applied to the subject for from 5 minutes to 24 hours in a day.

17. The method according to claim 10, wherein the subject has been diagnosed as having a condition selected from the group consisting of dementia, Alzheimer's disease, memory loss, inflammation, calcification, addiction, alcoholism, high blood pressure, aortic aneurysm recovery, lung regeneration, brain-immune interface difficulties, arthritis, vascular health, hypertension, vision recovery, teeth and gum regeneration, neurodegenerative disorders, hearing recovery, obesity, skin regeneration, aortic valve fibrosis, sun damage to the skin, psoriasis, depression and anxiety, aging, diabetic neuropathy, gut-brain health neurogenesis difficulties, pancreas and diabetes recovery, age-related inflammation, ALS, and/or Parkinson's.

18. The method according to claim 10, wherein the target tissue is muscle tissue.

19. A method, of using a bioelectric stimulator programmed to produce one or more bioelectric signals for stimulation of cellular tissue, wherein at least one such bioelectric signal downregulates expression of Klotho by the cellular tissue, the method comprising:
applying the bioelectric stimulator to target tissue of a subject, and
actuating the bioelectric stimulator to produce the one or more programmed bioelectric signals,
wherein the bioelectric stimulator is programmed with at least one bioelectric signal having a square, biphasic waveform at 50% duty and having a frequency selected from the group consisting of 25,000 Hz, 50,000 Hz, 750,000 Hz, and 1 MHz.

20. The method according to claim 19, wherein the bioelectric signal is applied to the subject for from 5 minutes to 24 hours in a day.

* * * * *